(12) United States Patent
Paulus et al.

(10) Patent No.: US 8,262,875 B2
(45) Date of Patent: Sep. 11, 2012

(54) SENSOR ARRANGEMENT AND METHOD FOR DETECTING A SENSOR EVENT

(75) Inventors: Christian Paulus, Weilheim (DE); Meinrad Schienle, Ottobrunn (DE); Claudio Stagni Degli Esposti, Bologna (IT); Roland Thewes, Gröbenzell (DE)

(73) Assignee: Siemens Aktiengesellschaft, Munich (DE)

( * ) Notice: Subject to any disclaimer, the term of this patent is extended or adjusted under 35 U.S.C. 154(b) by 862 days.

(21) Appl. No.: 11/663,078

(22) PCT Filed: Sep. 1, 2005

(86) PCT No.: PCT/DE2005/001536
§ 371 (c)(1),
(2), (4) Date: Mar. 16, 2007

(87) PCT Pub. No.: WO2006/029591
PCT Pub. Date: Mar. 23, 2006

(65) Prior Publication Data
US 2008/0036444 A1    Feb. 14, 2008

(30) Foreign Application Priority Data
Sep. 17, 2004   (DE) .................. 10 2004 045 210

(51) Int. Cl.
*B01J 8/20*   (2006.01)
(52) U.S. Cl. ............... 204/406; 205/792; 438/10
(58) Field of Classification Search .......... 204/400–435; 205/775–794.5; 438/10; 324/71.1
See application file for complete search history.

(56) References Cited

U.S. PATENT DOCUMENTS

| 5,294,889 | A | 3/1994 | Heep et al. |
| 6,170,318 | B1 | 1/2001 | Lewis |
| 6,380,747 | B1 * | 4/2002 | Goldfine et al. ............ 324/457 |
| 7,030,630 | B2 | 4/2006 | Haas et al. |
| 2002/0028441 | A1 | 3/2002 | Hintsche |
| 2002/0140440 | A1 | 10/2002 | Haase |
| 2003/0226768 | A1 * | 12/2003 | Hoffman et al. .......... 205/777.5 |
| 2005/0194250 | A1 | 9/2005 | Frey et al. |
| 2006/0216813 | A1 | 9/2006 | Gumbrecht et al. |
| 2006/0292708 | A1 * | 12/2006 | Frey et al. ...................... 438/10 |

FOREIGN PATENT DOCUMENTS

| DE | 196 10 115 A1 | 9/1997 |
| DE | 10218325 A1 * | 11/2003 |
| DE | 102 24 567 | 12/2003 |
| DE | 102 59 820 | 7/2004 |

(Continued)

OTHER PUBLICATIONS

U.S. Appl. No. 60/007,840.

(Continued)

*Primary Examiner* — J. Christopher Ball
(74) *Attorney, Agent, or Firm* — Harness, Dickey & Pierce, P.L.C.

(57) ABSTRACT

A sensor arrangement including a control circuit is disclosed. In at least one embodiment, at least one sensor electrode can be charged and/or discharged therewith and a comparator unit for the comparison of a provided voltage for the at least one electrode with a reference voltage. A duration necessary for the charging/discharging of the at least one sensor electrode is determined, whereby, from the determined duration, it is determined whether a sensor event, in the form of a hybridization between trap molecules and the particles for recording, has occurred.

15 Claims, 17 Drawing Sheets

FOREIGN PATENT DOCUMENTS

| | | |
|---|---|---|
| EP | 1 376 111 | 1/2004 |
| EP | 1 411 349 | 4/2004 |
| WO | WO 93/22678 | 11/1993 |
| WO | WO 03/065058 * | 8/2003 |

OTHER PUBLICATIONS

R. Hintzsche et al., "Microbiosensors using electrodes made in Si-technology", in "Frontiers in Biosensorics I—Fundamental Aspects", F.W. Scheller et al. ed., 1997, Birkhäuser Verlag Basel.

Christian Krause et al., "Capacitive Detection of Surfactant Adsorption on Hydrophobized Gold Electrodes", Langmuir, vol. 12, No. 25, 1996, p. 6059-6064.

Peter Van Gerwen et al., "Nanoscaled Interdigitated Electrode Arrays for Biochemical Sensors", Transducers '97, p. 907-910.

M. Riepl. M. Mirsky, S. Wolfbeis "Electrical Control of Alkanethiols Self-Assemply on a Gold Surface as an Approach for Preparation of Microelectrode Arrays", Mikrochim. Acta 131, 29-34 (1999).

M. Mirsky, M. Riepl, S. Wolfbeis, "Capacitive monitoring of protein immobilization and antigen-antibody reactions on monomolecular alkylthiol films on gold electrodes", Biosensors % Bioelectronics vol. 12, No. 9-10, pp. 977-989, 1997.

M. Paeschke, F. Dietrich, A. Uhlig, R. Hintsche "Voltammetric Multichannel Measurements Using Silicon Fabricated Microelectrode Arrays", Electroanalysis 1996, 8, No. 10.

* cited by examiner

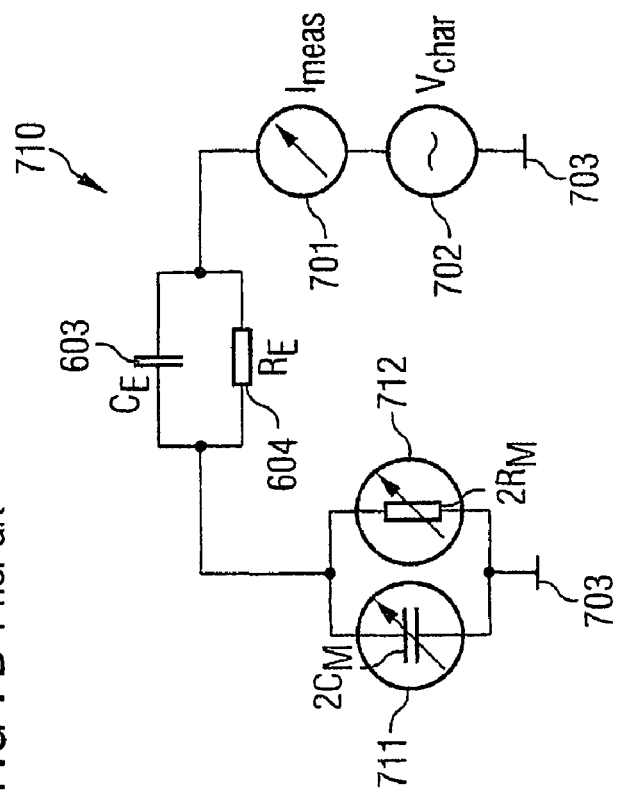
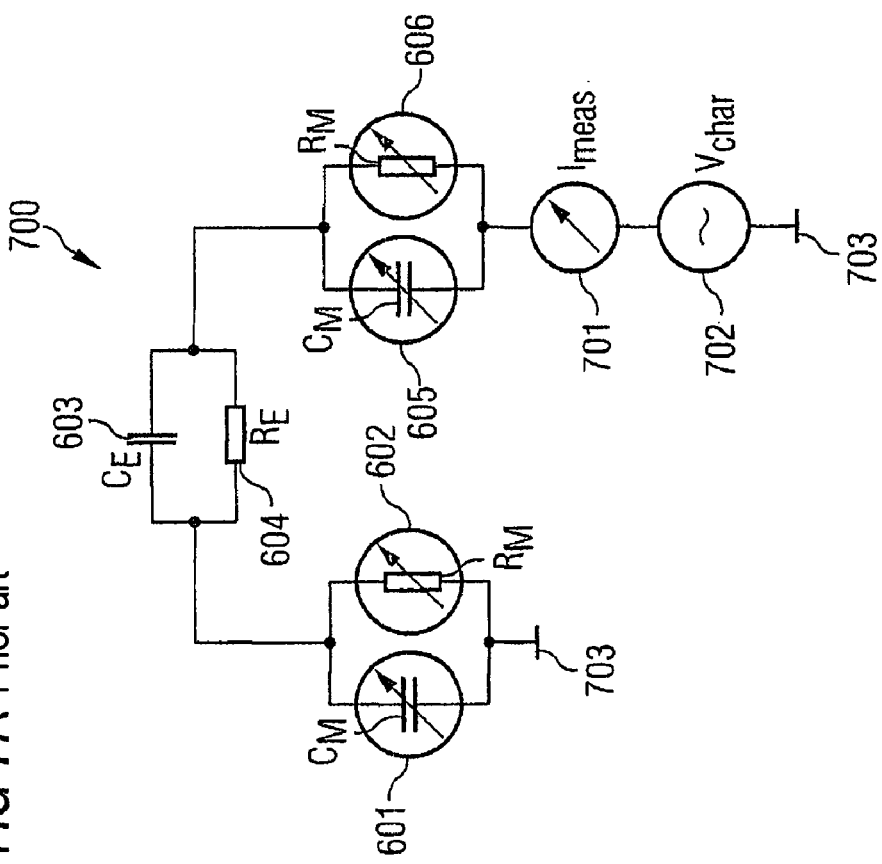
FIG 7A Prior art
FIG 7B Prior art

After immobilization

After hybridization

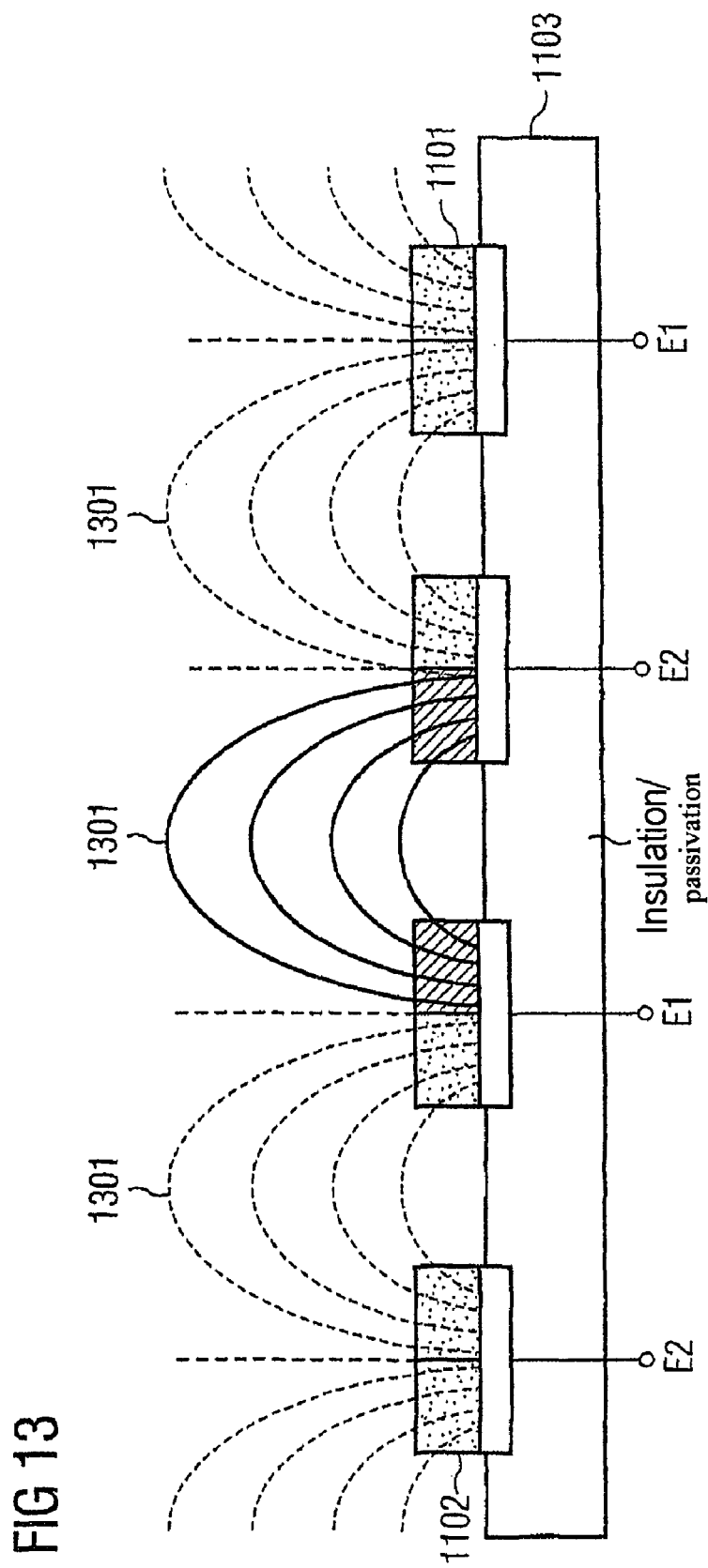

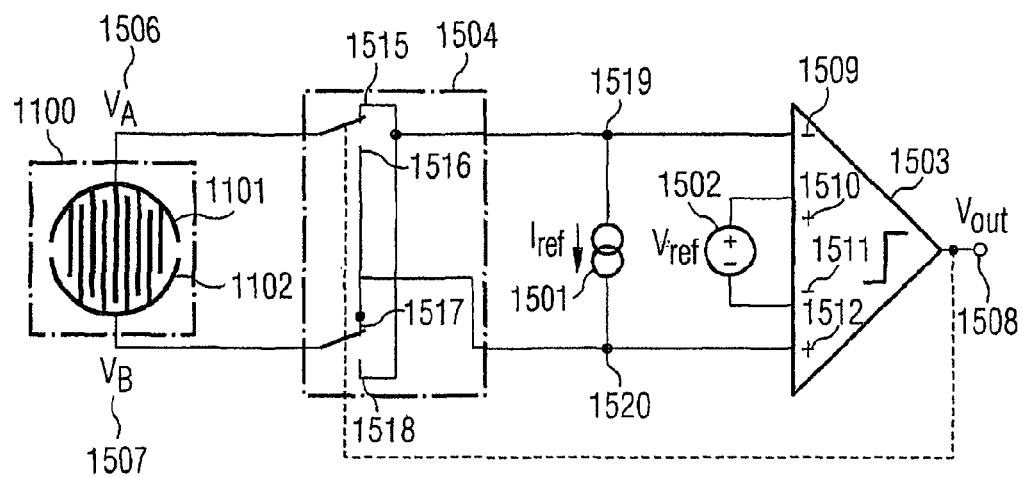

SENSOR ARRANGEMENT AND METHOD FOR DETECTING A SENSOR EVENT

PRIORITY STATEMENT

This application is the national phase under 35 U.S.C. §371 of PCT International Application No. PCT/DE2005/001536 which has an international filing date of Sep. 1, 2005, which designated the United States of America and which claims priority on German Patent Application number 10 2004 045 210.5 filed Sep. 17, 2004, the entire contents of which are hereby incorporated herein by reference.

FIELD

Embodiments of the invention generally relate to a sensor arrangement and/or a method for determining a sensor event.

BACKGROUND

Biosensor arrays and chemosensor arrays serve for detecting molecules in an analyte to be examined. Such arrays are increasingly being realized on chips for the purpose of miniaturization. The sensors are often arranged in a large number on a substrate. The substrate may be a semiconductor chip (silicon) for example, particularly for the case where functions of an integrated electronic circuit are intended to be realized.

Such substrates may alternatively be produced from glass, plastic or another material provided that no active electronics are required for operating them on the substrate. The high degree of parallelization enables a simultaneous parallel implementation of different tests, for example tests for the presence of different substances (e.g. molecules) in a predetermined analyte. On account of this property, such sensor arrangements including a corresponding evaluation system obtain diverse applications in medical diagnosis technology, in the pharmacological industry (e.g. for pharmacological screening, "high throughput screening", HTS), in the chemical industry, in foodstuffs analysis, and in ecological and foodstuffs technology.

The basic principle of many known sensors is based on the fact that firstly so-called catcher molecules are applied, e.g. using microdispensing techniques, and immobilized in a position-specific manner on a chip.

FIG. 1 shows a sensor arrangement 100 known from the prior art, in which a multiplicity of sensor arrays 102 are arranged in matrix-type fashion on a chip 101. The sensor arrays 102 are arranged in N columns and in M rows, that is to say at N×M positions, different catcher molecules being immobilized on each sensor array.

FIG. 2A to FIG. 2F in each case show a diagrammatic cross-sectional view of one of the sensor arrays 102 shown in FIG. 1. In particular, FIG. 2A to FIG. 2C show a first sensor array 200, and FIG. 2D to FIG. 2F show a second sensor array 201, the different illustrations of the first sensor array 200 in FIG. 2A to FIG. 2C corresponding to three different operating states, and the illustrations in FIG. 2D to FIG. 2F analogously corresponding to three different operating states of the second sensor array 201.

Each of the sensor arrays 200, 201 has a sensor electrode 202 integrated in the chip 101. First catcher molecules 203 are immobilized on the sensor electrode 202 of the first sensor array 200, the first catcher molecules 203 being DNA half strands. Second catcher molecules 204, which differ from the first catcher molecules 203, are immobilized on the sensor electrode 202 of the second sensor array 201.

FIG. 2A, FIG. 2D show the first sensor array 200 and the second sensor array 201, respectively, in an operating state in which the sensor arrangement 100 is free of potential binding partners (e.g. DNA half strands).

For the purpose of diagnosis, that is to say for examining an analyte for the presence of specific DNA molecules, an analyte 205 is firstly applied to all the sensor arrays 102 of the sensor arrangement 100 and therefore also to the sensor arrays 200, 201, i.e. the entire sensor arrangement 100 is flooded with the analyte 205 to be examined. This operating state of the first sensor array 200 is shown in FIG. 2B, and of the second sensor array 201 in FIG. 2E. Since the first catcher molecules 203 fit together with (half-stranded) DNA molecules present in the analyte 205, namely with the particles 206 to be detected, in accordance with the key/lock principle, a hybridization is effected, i.e. a binding of the respective DNA molecules 206 to the complementary first catcher molecules 203 of the first sensor array 200 (cf. FIG. 2B). Since the second catcher molecules 204 do not fit together with the particles 206 to be detected on account of their base sequence (cf. FIG. 2E), no hybridization is effected.

In order to obtain the operating states of the first sensor array 200 and of the second sensor array 201 respectively shown in FIG. 2C, FIG. 2F, the analyte 205 is removed from the sensor arrangement 100. Furthermore, a rinsing solution 207 is applied to the sensor arrangement 100. As a result, the particles 206 to be detected that have hybridized with the first catcher molecules 206 remain on the first sensor array 200, whereas only the second catcher molecules 204, but not particles 206 to be detected, remain on the second sensor array 201.

Optical methods are often used for detecting the hybridization that has taken place.

In an optical method, a fluorescent marker ("label") is bound to the DNA strands present in the analytes. If the entire sensor arrangement 100 is then irradiated with electromagnetic radiation (e.g. light) after a hybridization process that has taken place and after a further rinsing step, it is possible, on the basis of knowledge of the localization of the respective catcher molecules 203, 204, to determine the sensor arrays at which a hybridization has taken place (first sensor array 200) and the sensor arrays at which hybridization has not taken place (second sensor array 201). On the basis of the precise knowledge of the catcher molecules 203, 204 used, it is possible to deduce the presence or absence of specific particles to be detected in the analyte to be examined with a high selectivity. The optical methods have the disadvantage of needing a complicated and cost-intensive optical system for evaluation. This makes it more difficult for example to use such optical systems in physicians' practices, or in portable devices at all.

As an alternative to the optical method, a hybridization event that has taken place can be detected using an electric method.

In this respect, it is necessary to distinguish between methods based on the use of an enzyme label (described for example in [1], [2]) and so-called "label-free" methods, described for example in [3] to [9]. Label-free methods are more attractive since a method step for providing molecules with a label, which method step is often complicated from a biochemical standpoint, is avoided and a label-free method is therefore simpler in terms of sample preparation and hence less expensive.

However, the operation of an electronic biosensor is difficult to realize, so that, particularly in the case of the electronic label-free methods, hitherto examinations have been implemented only on individual sensors or on very small arrays comprising a stringing together of individual sensors.

Label-free methods known from the prior art are described below.

A first approach is disclosed in [3] to [6]. This approach is described below with reference to FIG. 3A to FIG. 7B.

FIG. 3A, FIG. 3B show an interdigital electrode arrangement 300 in which a first electrode structure 302 and a second electrode structure 303 are applied in a substrate 301, said electrode structures clearly meshing in interdigitated fashion. FIG. 3A shows a plan view of the interdigital electrode arrangement 300 and FIG. 3B shows a cross-sectional view along the section line I-I' shown in FIG. 3A. The interdigital electrode arrangement 300 contains periodic electrode components—arranged one beside the other—of the electrode structures 302, 303.

In order to explain the principle of the functioning of the interdigital electrode arrangement 300, a first partial region 304 of the interdigital electrode arrangement 300 will be described with reference to FIG. 4A, FIG. 4B.

The first partial region 304 is shown in a first operating state as a cross-sectional view in FIG. 4A and in a second operating state as a cross-sectional view in FIG. 4B.

Catcher molecules 400 are in each case immobilized on the electrode structures 302, 303. Gold material is preferably used for the electrode structures 302, 303, so that the immobilization of the catcher molecules 400 is realized using the particularly advantageous gold-sulfur coupling known from biochemistry, for example by a thiol terminal group (SH group) of the catcher molecules 400 being chemically coupled to the gold electrodes 302, 303.

An electrolytic analyte 401 to be examined, which is again intended to be examined for the presence of particles 402 to be detected (for example specific DNA molecules), is situated above the sensor electrodes 302, 303 during active sensor operation. A hybridization, that is to say a binding of DNA strands 402 to the catcher molecules 400, is effected only when the catcher molecules 400 and the DNA strands 402 match one another in accordance with the key/lock principle (cf. FIG. 4B). If this is not the case, then no hybridization is effected. The specificity of the sensor is thus derived from the specificity of the catcher molecules 400.

The electrical parameter that is evaluated in the case of this measurement is the complex electric resistance, i.e. the impedance 403 between the electrodes 302, 303, which is illustrated diagrammatically in FIG. 4A, FIG. 4B. On account of a hybridization that has taken place, the value of the impedance changes since the DNA particles 402 to be detected and the catcher molecules 400 comprise a material having electrical properties that deviate from the material of the electrolyte and, after the hybridization, the electrolyte is clearly displaced from the volume surrounding the electrodes 302, 303.

FIG. 5 shows a second partial region 305 of the interdigital electrode arrangement 300 in a cross-sectional view. The second partial region 305 represents a larger partial region of the interdigital electrode arrangement 300 than the first partial region 304 illustrated in FIG. 4A, FIG. 4B. FIG. 5 diagrammatically shows the profile of the electric field lines 500 between respectively adjacent electrode structures 302, 303.

As is furthermore shown in FIG. 5 the field profiles are periodic within a respective imaginary region through two lines of symmetry 501, so that the consideration of two directly adjacent electrode structures 302, 303 that is shown in FIG. 4A, FIG. 4B is sufficient. Furthermore, FIG. 5 diagrammatically shows a coverage region 502 for each of the electrode structures 302, 303, said coverage region representing the catcher molecules immobilized on the electrode structures 301, 302 and particles to be detected that have possibly hybridized with said catcher molecules. It can clearly be understood from the illustration shown in FIG. 5 that the profile of the field lines 500 is significantly influenced on account of a hybridization event since the physicochemical properties particularly of the coverage region 502 are altered.

It should furthermore be noted that, supplementarily or alternatively, catcher molecules may be provided in regions between electrodes 302, 303. The electrical properties of the electrodes or the electrode region again change in the case of hybridization events between catcher molecules provided in regions between the electrodes and particles to be detected.

FIG. 6 diagrammatically shows a simplified equivalent circuit diagram 600 of the first partial region 304 of the interdigital electrode arrangement 300 shown in FIG. 4A.

The equivalent circuit diagram 600 shows a variable first capacitance 601 $C_M$, the value of which is dependent on the extent of a hybridization effected at the electrode structure 302. A variable first nonreactive resistance 602 $R_M$ is connected in parallel with the capacitance. Clearly, the components 601, 602 represent the electrical properties of the surrounding region of the first electrode structure 302. The diagram furthermore shows a variable second capacitance 603 $C_E$ and a variable second nonreactive resistance 604 $R_E$ connected in parallel therewith, which represents the electrical properties of the analyte 401.

Moreover, the diagram shows a variable third capacitance 605 $C_M$ and a variable third nonreactive resistance 606 $R_M$ connected in parallel therewith, representing the electrical properties of the surrounding region of the second electrode structure 303. As is furthermore shown in FIG. 6, the parallel circuit comprising components 601, 602, the parallel circuit comprising components 603, 604 and the parallel circuit comprising components 605, 606 are connected in series. The components 601, 602, 605 and 606 are represented in variable fashion in order to illustrate that their values change on account of a sensor event.

In order to determine the value of the impedance, in one measuring method, an AC voltage $V_{char}$ is applied to one of the electrodes 302, 303, as shown in the equivalent circuit diagram 700 of the first partial region 304 shown in FIG. 7A. The AC voltage $V_{char}$ is provided using an AC voltage source 702. The current $I_{meas}$ flowing through the arrangement is detected using the ammeter 701. The components 701, 702 are connected in series with one another and are connected between the parallel circuit comprising components 605, 606 and the electrical ground potential 703. The AC current signal $I_{meas}$ resulting at the electrodes 302, 303 is evaluated together with the applied AC voltage $V_{char}$ in order to determine the impedance. As an alternative, in another measuring method a signal, that is to say an electrical voltage, may also be applied in each case to both electrodes 302, 303, the signals then being in antiphase.

The version of a simplified equivalent circuit diagram 710 shown in FIG. 7B differs from the equivalent circuit diagram 700 shown in FIG. 7A in that the elements $C_M$ 601, 605 and $R_M$ 602, 606 have been combined to form a first effective capacitance 711 and, respectively, to form a first effective nonreactive resistance 712.

The distance between the electrodes 302, 303 and the width of the electrodes is typically in the sub-μm range. In accordance with the interdigital electrode arrangement 300, a multiplicity of electrode components (clearly fingers) of the electrode structures 302 and 303 are arranged parallel to one another. Circular arrangements are used in [3] to [6] for reasons of surface functionalization. The external dimensions or the diameter of such individual sensors is typically in the range of from approximately 100 μm to several hundreds of μm.

With regard to the exciting AC voltage $V_{char}$, it should be taken into account that its root-mean-square value or its peak value ought not to exceed a specific maximum value. The biochemical or electrochemical boundary conditions enabling the operation of such sensors are violated when such a maximum value is exceeded. If the electrode potential (which is referred to the electrical potential of the electrolyte) exceeds an upper threshold value, then specific substances may be oxidized in a surrounding region of an electrode. If the electrical potential (which is referred to the electrical potential of the electrolyte) falls below a lower threshold value, substances are reduced there.

An undesirable oxidation or reduction may have the effect, inter alia, of breaking up the chemical bonds entered into during immobilization and hybridization. Furthermore, electrolysis may commence at the sensor electrodes, so that the electrolysis products bring the chemical milieu required for operation of the sensors out of the required equilibrium or lead to gas formation. The absolute values of the critical potentials depend on the composition and the concentration ratio and the chemical surroundings of the electrodes (for example an immobilization layer, an analyte, etc.).

Typical values for the exciting voltage lie in the range of a few 10 mV to at most around 100 mV. This is an important boundary condition for the operation of such sensors since the resulting measurement signal (current intensity $I_{meas}$), with regard to its magnitude, is approximately directly proportional to the applied voltage.

A second principle of a label-free electrical sensor such as is disclosed in [7] to [9] is described below with reference to FIG. 8 to FIG. 10.

In accordance with this second approach, a planar electrode is in each case used for the detection of a species, that is to say for the immobilization of catcher molecules and for hybridization with particles to be detected. Furthermore, an AC voltage signal is applied directly to an electrically conductive analyte. In the case of these methods, the application of the AC voltage and the optionally required additional application of a DC offset are effected using a so-called counterelectrode or reference electrode, which realizes a low-impedance electrical coupling to the electrolyte, which electrical coupling is always defined under changing electrochemical conditions and is constant in terms of its electrical properties. Such a reference electrode is usually produced from a different material (for example silver/silver chloride) than the electrodes that are utilized for immobilizing the catcher molecules and are therefore often produced from gold material. The use of different materials results from the different electrochemical requirements made of the two electrode materials.

FIG. 8A, FIG. 8B show a sensor arrangement 800 in accordance with this second approach. FIG. 8A shows a plan view of the sensor arrangement 800 and FIG. 8B shows a cross-sectional view along a section line II-II' from FIG. 8A.

As is shown in FIG. 8A, a plurality of sensor arrays 802 and a common reference electrode 803 are arranged on a silicon substrate 801. Provided on the surface of each sensor array 802 is an active region 805, on which catcher molecules are immobilized, for hybridization with complementary particles to be detected. An analyte 804 is filled into the sensor arrangement 800. The sensor arrangement 800 uses a silicon substrate 801, although the electrical properties of the silicon are not utilized, in order to form powerful integrated electronics therein.

FIG. 9 shows an equivalent circuit diagram 900 of a partial region 806 of the sensor arrangement 800. This shows a variable first capacitance 901 $C_M$, which represents the capacitance of the surrounding region of the sensor array 802. Furthermore, a variable first nonreactive resistance 902 $R_M$ connected in parallel therewith is shown, representing the nonreactive resistance of the surrounding region of the sensor array 802. A variable second capacitance 903 $C_E$ and a variable second nonreactive resistance $R_E$ 904 connected in parallel therewith represent the electrical properties of the analyte 804.

Furthermore, FIG. 10 shows a further equivalent circuit diagram 1000 of the partial region 806 of the sensor arrangement 800. The latter exhibits, in addition to the components shown in FIG. 9, an AC voltage source 1002, by which an AC voltage can be applied, and exhibits an ammeter 1001 for detecting a measurement current $I_{meas}$. The components 1001, 1002 connected in parallel are connected between the electrical ground potential 1003 and the parallel circuit comprising components 903, 904.

Often only very small sample volumes are available in biochemistry. In this case, the use of the sensor arrangement 800 is disadvantageous since the counterelectrode 803 can be provided in miniaturized form only in a very complicated manner, or not at all. It is often realized by a small chlorinated silver tube.

In the case of the described sensor arrangements known from the prior art, the problem occurs during operation or evaluation of measurement signals that the impedance between the electrodes does not have exclusively capacitive components, but rather is a relatively complex, composite quantity. A fundamental reason for this is that, at the measurement electrode, that is in direct electrical (galvanic) contact with the electrolyte, an electrochemical conversion always takes place which is at equilibrium only precisely when the electrical potential of the electrode with respect to the electrolyte can be set freely. Any displacement of this electrical potential automatically results in a net conversion of material at the electrodes which, metrologically, is manifested as an approximately ohmic conductivity.

The immobilization of catcher molecules in principle influences the material conversion at the electrode surface since the electrode is partially covered thereby, and on account of specific electrical properties of the molecules (for example on account of the fact that DNA molecules are often present as polyanions). This makes it more difficult for the detected sensor signals to be evaluated metrologically. Therefore, it is attempted to configure the measurement in such a way that only the value of the electrode capacitance $C_E$ that is dependent on the hybridization in the equivalent circuit diagrams specified is determined. As an alternative, it is possible to measure magnitude and phase of the impedance as a function of the exciting frequency, so that ideally all parameters can be determined from the resulting Bode diagram. However, this procedure is very complicated.

One possibility for obtaining signals that can be evaluated in an improved manner consists in the use of a so-called lock-in amplifier for detecting the sensor signal. This principle is explained below on the basis of the equivalent circuit diagrams 900, 1000 shown in FIG. 9, FIG. 10.

With the aid of a lock-in measuring device, an AC voltage $V_{char}$ with a frequency f is applied to the electrolyte 804 via the counterelectrode 803 which ensures a low-impedance connection to the electrolyte 804. It is then possible to measure the imaginary part and the real part of the complex total current $I_{meas}$ resulting from the elements $C_M$, $R_M$, $C_E$ and $R_E$.

Assuming that the magnitude of the complex impedance component of the electrolyte 804, namely $1/(2\pi f C_E)$, is significantly greater than the magnitude of the purely resistive component $R_E$, the measured current results as:

$$I_{meas} = V_{char} \times \cfrac{1}{R_E + \cfrac{R_M \times \frac{1}{j2\pi f C_M}}{R_M + \frac{1}{j2\pi f C_M}}} \quad (1)$$

The imaginary part of the current amounts to:

$$\mathrm{Im}(I_{meas}) = V_{char} \times \frac{2\pi f C_M}{\left(\frac{R_E}{R_M} + 1\right)^2 + 4\pi^2 f^2 C_M^2 R_E^2} \quad (2)$$

Under the further assumption that the nonreactive resistance of the electrolyte $R_E$ is significantly less than the parasitic sensor parallel resistance $R_M$, that is to say if $R_M \gg R_E$ holds true, and assuming that the frequency f is chosen to be sufficiently low, so that $$4\pi^2 f^2 C_M^2 R_E^2 \ll 1 \quad (3)$$

is satisfied, then to an approximation the simple relationship $$\mathrm{Im}(I_{meas}) = V_{char} \times 2\pi f C_M \quad (4)$$

can be specified for equation (2). Equation (4) clearly states that the imaginary part of the current that is determined by means of the lock-in method depends linearly on the sensor capacitance $C_M$.

It is only under these conditions that the precise change of $C_M$ comprises the information sought.

The need to satisfy equation (3) sufficiently well upwardly limits the choice of measurement frequency. However, the free choice of a frequency that is not all that low is desirable since in accordance with equation (4) the magnitude of the measurement signal to be evaluated rises proportionally with the frequency. In order to obtain a signal that can be evaluated well in accordance with equation (4) even in the case of the low frequencies and the stipulations for the order of magnitude of the voltage $V_{char}$, it is necessary to use either large-area sensors, which lead to large values for the sensor capacitance $C_M$, or highly sensitive amplifiers, which is complicated.

The use of a lock-in amplifier has a considerable disadvantage despite the improved detection sensitivity. Complex circuit arrangements are required for the driving and evaluation, said circuit arrangements requiring a considerable space requirement despite a miniaturization of the sensor arrangement compared with the arrangements known from the prior art, with the result that only a limited number of said sensor arrangements can be arranged in matrix-type fashion on the chip area.

Document [10] discloses a method for detecting an analyte, wherein an integrated system is provided which has a sensor arrangement having a plurality of different sensors, wherein each sensor has a matrix composed of alternately conductive and nonconductive regions. When the analyte is present, the electrical resistance of the sensor arrangement changes. This temporal change in the electrical resistance is measured and compared with stored data, the requisite memory unit and the processing unit being integrated in the substrate of the sensor arrangement. The temporal profile of the measurement curve of the resistance values is dependent on the permeation of the sensor arrangement by the analyte. This specific property of the analyte is utilized for detection.

SUMMARY

At least one embodiment of the invention is based on the problem of providing a sensor arrangement in accordance with the impedance method with simple sensor event identification.

The problem is solved by way of a sensor arrangement and/or a method of at least one embodiment for determining a sensor event.

A sensor arrangement of at least one embodiment has a sensor element having at least one electrode, the electrode preferably having a comb-type structure. Furthermore, the sensor arrangement has a drive circuit, which is set up in such a way that a predetermined current is provided, and that the at least one electrode is charged and/or discharged with the predetermined current.

In an alternative configuration of at least one embodiment the invention, it is provided that two electrodes, which are at the same electrical potential, are arranged such that they intermesh in comb-type fashion, and that a third electrode, which is at a different electrical potential, is arranged in meandering fashion between the two electrodes having the same electrical potential.

The sensor element is set up in such a way that an electrical voltage dependent on a sensor event in terms of its profile is provided at the at least one electrode.

The sensor arrangement is set up in such a way that a time duration required for the charging and/or discharging of the at least one electrode to a specific voltage value is determined.

According to of at least one embodiment the invention, the sensor arrangement has a comparator unit, wherein the comparator unit is set up in such a way that the electrical voltage provided by the electrode, which voltage corresponds to a charging operation and/or discharging operation and has a temporal voltage profile dependent on a sensor event, is compared with a predetermined reference voltage. The comparator unit preferably has a comparator. Furthermore, a voltage source coupled to the comparator unit is provided, which voltage source provides a reference voltage. Furthermore, the comparator unit is set up in such a way that the comparator compares the potential difference between the reference voltage and the electrical voltage provided by the sensor element during the charging operation and/or discharging operation of the at least one electrode, preferably continuously.

Clearly, the value of a capacitance is determined depending on the predetermined electric current and a time duration required for the charging and/or discharging of the at least one electrode, the time duration for the charging and/or discharging being dependent on a sensor event.

A method for determining a sensor event is furthermore provided in at least one embodiment. In accordance with at least one embodiment of the method, a voltage dependent on a sensor event in terms of its temporal profile is provided by a sensor element. Furthermore, a predetermined current is provided by a drive circuit, at least one electrode being charged and/or discharged with the predetermined current.

In accordance with the method of at least one embodiment of the present invention, the voltage provided by the sensor element during a charging operation and/or discharging operation is compared with a reference voltage, the comparator unit outputting a comparison result in the form of a signal. In the method, moreover, the time duration required for the charging and/or discharging of the at least one electrode of the sensor element is determined, the time duration for the charging and/or discharging being dependent on a sensor event. Furthermore, in accordance with at least one embodiment of the method, the time duration is used to determine whether or not a sensor event has taken place or the extent to which a sensor event has taken place at the sensor element.

Clearly, at least one embodiment of the invention provides a multi-analysis system for the qualitative and quantitative evaluation of the analysis of macromolecular biomolecules, e.g. proteins, and in particular of DNA half strands. The simplification of the switching electronics makes it possible to integrate the sensor arrangement in an array by means of CMOS technology, whereby the detection sensitivity is improved by the minimization of parasitic voltages and currents.

A basic idea of at least one embodiment of the invention is to be seen in the fact that a sensor arrangement having a multiplicity of sensor electrodes is provided on a substrate. Before and after a sensor event, for example a hybridization between catcher molecules and DNA half strands situated in an analyte, contrary to the prior art in [3] and [9], a predetermined, preferably constant, electric current is fed to or passed from a selected electrode, whereby the selected electrode is charged or discharged. For the charging operation, a switch unit is brought to a first switch position, as a result of which a current flows in the positive flow direction through the electrode. After the charging operation, by way of a second switch position, wherein a current thereby flows in the negative flow direction through the electrode, the at least one electrode is discharged independently of whether or not a sensor event has taken place.

According to at least one embodiment of the invention, for this purpose, the current flow direction and also the direction of the reference potential are inverted by way of a switch unit, the switch state of the switch unit being changed over by way of a control unit. The signals necessary for the changeover of the switch unit are generated by a control unit. Consequently, a current now flows in the negative direction through the selected electrode and a negative potential is likewise present at the selected electrode.

Owing to a sensor event, the value of the impedance, in particular the value of the capacitance, between the selected electrode of the sensor element and at least a portion of the other electrode of the sensor element changes according to a hybridization event. According to at least one embodiment of the invention, the time duration required for the charging and/or discharging of the at least one electrode is taken as a basis for determining whether a sensor event for example in the form of a hybridization event, generally a complexing event, or some other sensor event, for example in the form of a direct change in conductivity as a consequence of the metabolism of cells immobilized on the electrodes, has occurred.

Clearly, it is proposed to use an array configuration having a multiplicity of sensor electrodes. Catcher molecules are applied and immobilized on the electrodes and/or between the electrodes, that is to say bonded to the sensor surface, in a manner known per se, for example using microdispensing techniques. The use of a reference electrode, as described above with reference to FIG. 8A to FIG. 10, is avoided according to at least one embodiment of the invention. Consequently, the need for a special, problematic electrode material for such a reference electrode is also obviated.

Clearly, at least one embodiment of the invention provides a novel array architecture, a new driving and a new possibility for evaluation of the sensor electrodes.

The realization of such arrays on a semiconductor chip as a substrate affords the advantage that it is possible to realize a sensor arrangement with a significantly higher number of individual sensor electrodes in conjunction with a reduced area. This leads on the one hand to a significantly higher number of tests that can be implemented temporally in parallel by means of such a sensor arrangement and on the other hand to a significantly higher number of parameters that can be characterized simultaneously. Furthermore, it is possible to reduce the volume of chemical reagents required for the operation of such sensor arrangements.

A further advantage is that it is possible to use a significantly smaller area for the sensor electrodes, compared with the electrode configurations in accordance with the prior art. The smaller signal amplitude on active semiconductor chips, i.e. semiconductor chips with drive and evaluation electronics integrated in the substrate, that is governed by the smaller sensor area of the individual sensors is not a disadvantage compared with a passive realization i.e. sensor chips with external drive and evaluation electronics since, in a monolithically integrated sensor arrangement, this signal can be amplified "on-chip" with the aid of circuits that are integrated for example below the sensor electrodes in the substrate. Consequently, such chips are able to supply a better signal-to-noise ratio of the sensor signals to be evaluated.

In particular, the tolerance of such chips in relation to interference signals coupled in externally is significantly greater than in the case of using passive electrical sensor arrays in which comparatively long electrical lines have to be coupled to the measuring equipment. Signals passed on these lines are sensitive to interference coupling into the lines on account of their small amplitude. Furthermore, the parasitic capacitance of the lines is large in comparison with the sensor capacitance of small sensor structures, with the result that the detection sensitivity is reduced.

A further advantage, particularly in comparison with the reference electrode arrangement described with reference to FIG. 8 to FIG. 10, is that the technological requirements made of the materials to be used are much lower. In particular, the need to provide a reference electrode, which is often realized as a silver/silver chloride electrode, for producing an electrochemical reference potential with respect to the electrodes is avoided.

The sensor arrangement may be set up in a manner for determining, for at least a portion of the sensor electrodes, sequentially in each case for a selected sensor electrode whether or not a hybridization event has taken place at the respectively selected sensor electrode. In other words, it is possible successively to select a plurality of sensor electrodes in order to determine whether or not a sensor event has taken place at said sensor electrodes, in which case a different analysis can be carried out in each sensor arrangement.

At least one embodiment of the invention is distinguished, in particular, by the fact that a lock-in amplifier can be dispensed with, and by the fact that according to at least one embodiment of the invention, each sensor element can be selectively driven and evaluated. A further advantage of at least one embodiment of the present invention is the very simple and space-saving respective switching structure of the drive circuit, of the comparator unit and of the evaluation circuit. This enables the sensor arrangement to be integrated into a substrate with CMOS technology.

A sensor arrangement according to at least one embodiment of the invention in accordance with a further example embodiment of the invention is described below. The configurations of the sensor arrangement in accordance with a first example embodiment of the invention also hold true for the sensor arrangement in accordance with the second example embodiment of the invention.

A sensor arrangement having at least one electrode of the sensor element that is provided on a substrate is provided in accordance with the second example embodiment of the invention. Catcher molecules set up in such a way that particles to be detected can hybridize with them are immobilized on the at least one electrode.

According to at least one embodiment of the invention, the sensor element of the second example embodiment of the invention likewise has a comb-type structure.

According to at least one embodiment of the invention, the drive circuit in accordance with the second example embodiment of the invention has a first current source and a second current source for the charging and/or discharging of the at least one electrode, wherein a choice is made between a charging operation and/or discharging operation by way of the changeover of the switch state of the first switch unit. A reference voltage is applied to the other electrode of the interdigital structure, in which case the reference voltage may be a constant voltage, for example the ground potential, alternatively a temporally variable reference voltage, which is preferably independent of a sensor event.

The device in accordance with the second embodiment of the invention has two voltage sources of opposite polarity. By way of a second switch unit between the voltage sources and the comparator, switching is carried out according to the cycles between the two voltage sources. Moreover, the comparator unit in accordance with the second embodiment has a comparator that compares the potential of the at least one electrode with the reference potential.

In accordance with a further example embodiment of the invention, the two current sources which are provided in accordance with the second embodiment of the invention may be replaced, according to at least one embodiment of the invention, by in each case a nonreactive or else nonlinear resistance.

In accordance with a further example embodiment of the invention, the drive circuit may be arranged between the sensor element and the comparator unit. The switch unit for the respective changeover of the current flow direction through the at least one electrode is arranged between the drive circuit and the sensor element. This arrangement is advantageous since a reduction of the switching operations is obtained since the current source and the reference voltage source are no longer changed over periodically by means of the switch unit, but rather the electrodes of the sensor element by means of a switch unit.

The method according to at least one embodiment of the invention for determining a sensor event at a sensor element is described in more detail below. Configurations of the sensor arrangement also hold true for the method for operating the sensor arrangement.

One aspect of at least one embodiment of the invention can be seen in a repeated changeover between a charging operation and/or discharging operation of an interdigital electrode. The interdigital electrode preferably has a comb-type structure.

According to at least one embodiment of the invention, the two electrodes of the interdigital electrode of the sensor element are charged and/or discharged in antiphase by means of a preferably constant current having a respectively opposite sign. This results in a potential difference between the two electrodes, which potential difference is continuously compared with a reference potential of the at least one reference voltage source. If, upon comparison, the voltage of the at least one electrode of the sensor element corresponds to and/or exceeds the value of the reference potential, then the current respectively present at the two electrodes is, according to the invention, inverted in contrast to the preceding charging operation and/or discharging operation.

As an alternative, a clocked comparison—defined at specific instants—of the potential difference with the reference potential is also possible.

The comparator unit preferably has a comparator which is coupled to a reference voltage source and which compares the potential difference with the reference potential. After a changeover operation, an electrical signal is communicated to an evaluation circuit by way of the comparator. The evaluation circuit may either be integrated in the sensor element and have a counting device, for example, or the output signal of the comparator is switched by selection of the sensor element directly onto a read-out line, which forwards the digital output signal of the comparator to peripheral circuits of the sensor matrix. The peripheral circuits then determine the required time duration for the charging and/or discharging of the electrodes of the sensor element of two successive changeover operations, wherein a respective one of the two electrodes is charged within one cycle, while the other is discharged.

According to at least one embodiment of the present invention, each sensor arrangement can be operated sequentially; therefore, a counting device is not absolutely necessary. Digital circuits are used for the sequential operation, which digital circuits generate corresponding selection, activation and deactivation signals in order to control the respective sensor element.

The counting device counts the temporally successive signals of the comparator in a predeterminable time interval, which results in a frequency f and a required time duration T corresponding to a direct measurement of the impedance value can be determined in accordance with the following equation:

$$\frac{1}{f} = T = 2R_{sensor}C_{sensor}\ln\frac{1}{1-\frac{V_{ref}}{I_{ref}R_{sensor}}}. \qquad (5)$$

The variables that are essential for a cycle are $R_{sensor}$ and $C_{sensor}$, which directly represent the impedance of the sensor element, where $V_{ref}$ is the voltage of the reference voltage source and $I_{ref}$ is the charging and/or discharging current of the electrodes.

The value of the impedance is composed of a resistive component and a capacitive component. The characteristic information about a sensor event is essentially contained in the capacitive component of the measured impedance. However, the value of the resistive component is contained in the signal obtained from the measurement. Consequently, it is necessary to apply a method to filter out the capacitive component from the signal obtained from the measurement.

By varying the charging and/or discharging current of the electrodes, either the resistive or the capacitive component is obtained. For $I_{ref} \to 0$, the resistive component essentially contributes to the signal. For $I_{ref} \to \infty$, the capacitive component critically contributes to the signal. In order to determine the resistive component and also the capacitive component for an unambiguous measurement result according to the invention, a function for T that is dependent on $I_{ref}$ is expedient. The capacitive component is then determined from this by way of the following equation:

$$C = -\frac{1}{2V_{ref}\frac{\partial}{\partial I_{ref}}\left[\left(I_{ref}\frac{\partial T}{\partial I_{ref}}\right)^{-1}\right]}. \qquad (6)$$

Clearly, at least one embodiment of the invention affords a possibility of providing and operating a simplified and highly accurate sensor arrangement using the impedance method.

Furthermore, the sensor architecture can be used for any desired detection technique. Purely resistive or purely capacitive measurement methods are also conceivable. The coating of the sensor electrode has to be changed according to the respective measurement method. For a DNA sensor, by way of example, individual DNA strands that are complementary to the particles to be detected are applied to the sensor electrodes.

In accordance with one configuration of at least one embodiment of the invention, the sensor event determining unit is set up in such a way that a charging frequency and/or a discharging frequency or a cycle frequency, where a cycle in each case has a charging operation and a discharging operation, is determined from the determined time durations of the charging operation and/or of the discharging operation.

Furthermore, the sensor architecture can also be used for the detection of chemical substances, such as e.g. solutions and gases. For the detection of substances in chemical solutions, it is advantageous for the coating of the sensor element to be set up in such a way that it is reactive toward the substance to be detected, in order to be able to determine changes in a dielectric constant, a conductivity or an impedance value. If the sensor element is operated as a liquid sensor, the electrodes need not necessarily be in direct contact with the liquid to be analyzed. A dielectric material that is inert to the liquid is preferably applied on the electrodes. The sensor coating is then applied on said inert dielectric layer. However, this gives rise to a higher outlay for determining an impedance value, for example, since the electrodes are insulated from the analyte by the dielectric layer.

Drive electronics and simple evaluation electronics are clearly provided, so that a plurality of sensor arrangements can be arranged in parallel, in which the sensor elements are arranged in matrix-type fashion. This results in a sensor array having a high detection sensitivity since, for each sensor arrangement, simple drive electronics and evaluation electronics can be realized using CMOS technology, which results in an advantage of a lower susceptibility to interference signals.

The immobilization region of the first electrode can be coated with a material which can immobilize catcher molecules.

The immobilization region can therefore have for example one of the following materials:
  hydroxyl radicals,
  epoxide radicals,
  amine radicals,
  acetoxy radicals,
  isocyanate radicals,
  succinimidyl ester radicals,
  thiol radicals,
  gold,
  silver,
  platinum,
  titanium,
  palladium,
  silicon dioxide,
  silicon nitride.

The immobilization region can be configured both for holding ligands with which peptides or proteins can be immobilized, and for holding DNA catcher molecules with which DNA molecules can be immobilized.

According to at least one embodiment of the invention, the sensor arrangement or the sensor element serves for the detection of biomolecules, biopolymers or else macromolecular biopolymers, or the sensor arrangement or the sensor element is set up in such a way that biomolecules, biopolymers or else macromolecular biopolymers can be detected.

Macromolecular biopolymers are to be understood to mean for example proteins or peptides or else DNA strands having a respectively predetermined sequence.

If proteins or peptides are to be detected as macromolecular biopolymers, then the immobilized molecules are ligands, for example active substances having a possible binding activity, which bind the proteins or peptides to be detected to the respective electrode on which the corresponding ligands are arranged.

The suitable ligands include enzyme agonists or enzyme antagonists, pharmaceuticals, sugars or antibodies or any molecule which has the capability of specifically binding proteins or peptides.

If the macromolecular biopolymers used are DNA strands having a predetermined sequence which are intended to be detected by way of the biosensor, then it is possible, by way of the biosensor, for DNA strands having a predetermined sequence to be hybridized with DNA catcher molecules having the complementary sequence with respect to the sequence of the immobilized DNA strands as molecules on the first electrode.

In the context of this description, a catcher molecule is to be understood to mean both a ligand and a DNA catcher molecule.

The immobilization region can be configured for holding catcher molecules with which peptides or proteins can be immobilized.

As an alternative, the immobilization region can be configured for holding DNA catcher molecules with which DNA molecules can be immobilized.

BRIEF DESCRIPTION OF THE DRAWINGS

Example embodiments of the invention are illustrated in the figures and are explained in more detail below.

In the figures:

FIGS. 7A, 7B show equivalent circuit diagrams of the first partial region of the interdigital electrode arrangement in accordance with the prior art as shown in FIG. 3, FIGS. 8A, 8B show a plan view and a cross-sectional view along the section line II-II' of a sensor arrangement with reference electrode in accordance with the prior art, FIG. 13 shows a diagrammatic cross-sectional view of the interdigital structure and the electric field of adjacent fingers of the electrodes, FIG. 20 shows a sensor arrangement in accordance with a fourth embodiment of the invention.

DETAILED DESCRIPTION OF THE EXAMPLE EMBODIMENTS

Figure 11:
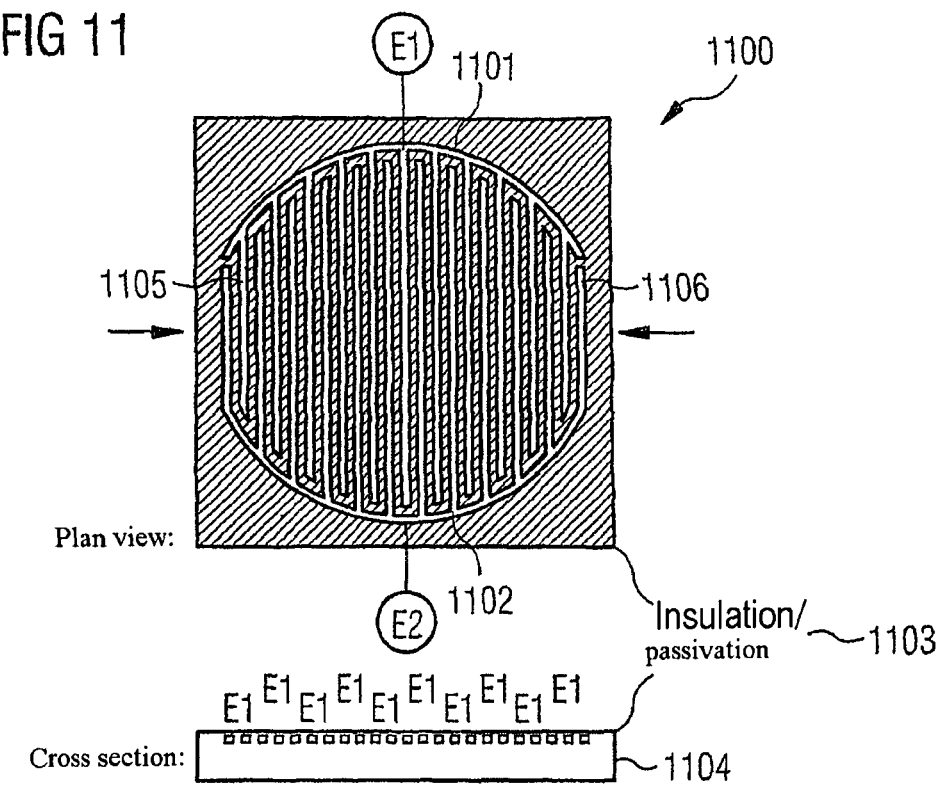
FIG. 11 shows a plan view of the sensor element having a comb-type structure, wherein the sensor element is an interdigital structure, and a schematic cross-sectional view of the interdigital structure.

A description is given below, with reference to FIG. 11, of a sensor element 1100 in accordance with a first embodiment of the invention.

The sensor element 1100 has a first electrode 1101 and a second electrode 1102, the first electrode 1101 and the second electrode 1102 having a comb-type structure. The fingers of the first electrode 1101 and of the second electrode 1102 are intermeshed in one another. Furthermore, the sensor element 1100 has an insulation layer or passivation layer 1103, on which the first electrode 1101 and the second electrode 1102 are arranged. FIG. 11 furthermore shows a diagrammatic cross-sectional view 1104 of the sensor element 1100, wherein the intermeshed structure of the fingers 1105 of the first electrode 1101 with the fingers 1106 of the second electrode 1102 can be seen.

A description is given below, with reference to FIGS. 12a and 12b, of a sensor arrangement in accordance with a first embodiment of the invention.

Figure 12A:
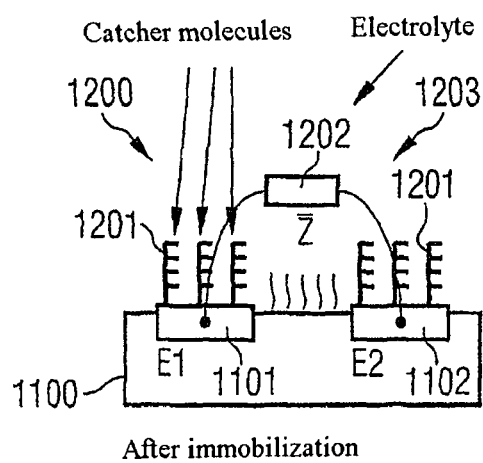
FIG. 12a shows a diagrammatic cross-sectional view of a detail from the interdigital structure of adjacent electrodes with catcher molecules immobilized on the electrodes.

FIG. 12a shows a part 1200 of a diagrammatic cross-sectional view of the sensor element 1100 after immobilization of catcher molecules has been effected. E1 designates a finger of the first electrode 1101 and E2 designates a finger of the second electrode 1102. Catcher molecules 1201 are immobilized on the fingers of the respective electrode, in which case, in accordance with the prior art, catcher molecules can also be immobilized between the individual fingers of the electrodes. The value of an impedance Z 1202 between the first electrode 1101 and the second electrode 1102 is determined in accordance with the method of an embodiment of the invention.

Figure 12B:
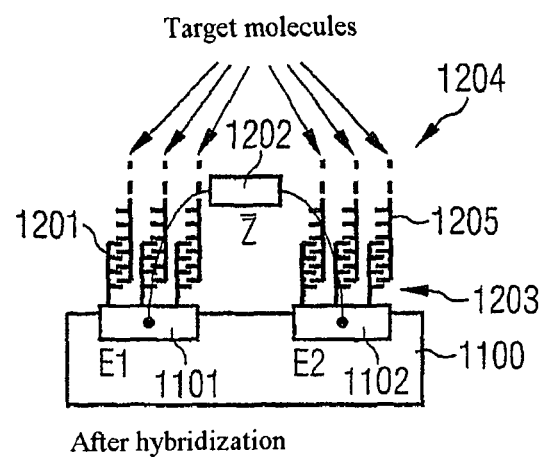
FIG. 12b shows a diagrammatic cross-sectional view in accordance with the arrangement from FIG. 12a after a hybridization event.

FIG. 12b shows a part 1204 of a diagrammatic cross-sectional view of the sensor element 1100 after a hybridization event, e.g. DNA semiconductor strands 1205 hybridizing with the catcher molecules 1201.

Clearly, the value of the electrical impedance between the selected sensor electrode 1101 and the electrolyte 1203 changes owing to a sensor event, that is to say a hybridization between first catcher molecules 1201 and DNA half strands 1205 to be detected on the first sensor electrode 1101. This is clearly attributable to the fact that, on account of the hybridization event, electrolyte liquid with comparatively good electrical conductivity and a high dielectric constant is displaced from a surrounding region of the selected sensor electrode 1101 and is replaced by DNA half strands 1205 with different electrical properties than the electrolyte 1203. This results in a change in the value of the impedance 1202, and in particular the value of the capacitance between the first electrode 1101 and the second electrode 1102, since both the DNA half strands 1205 and the catcher molecules 1201, as organic molecules, usually have a lower electrical conductivity and dielectric constant compared with the electrical properties of the electrolyte 1203.

The alteration of the impedance 1202 and therefore the quantity of hybridization events that have taken place on the first sensor electrode 1101 can be deduced from the altered capacitance. Therefore, the alteration of the impedance is a measure of the concentration of the DNA half strands 1205 in the analyte 1203, so that the value of the concentration can be determined.

In the case of the sensor arrangement 1100, clearly one and the same sensor electrode functions as selected sensor electrode or as counterelectrode in different operating states.

FIG. 13 shows a diagrammatic cross-sectional view of the sensor element 1100 and a general profile of the field lines 1301 of the electric field between the fingers 1105, 1106 of the electrodes 1101, 1102 of the sensor element 1100.

A description is given below, with reference to FIG. 14, of a diagrammatic cross-sectional view of the interdigital structure of the sensor element and an equivalent circuit diagram of the resistance and capacitance values of the electrolyte and the relatively close surroundings of the electrodes.

Figure 14:
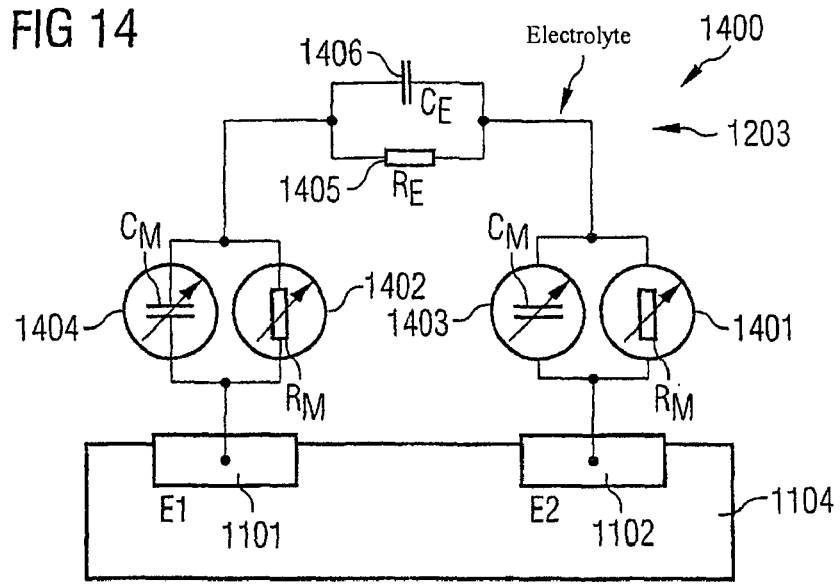
FIG. 14 shows a diagrammatic cross-sectional view of the interdigital structure and an equivalent circuit diagram for the resistance and capacitance values of the electrolyte and an equivalent circuit diagram for the resistance and capacitance values of the relatively close surroundings of the electrodes.

The arrangement 1400 in accordance with FIG. 14 shows adjacent electrode structures of the first electrode 1101 and of the second electrode 1102 of the sensor element 1100, variable equivalent resistances $R_M$ 1401, 1402 and variable equivalent capacitances $C_M$ 1403, 1404, which represent the electrical properties of the surrounding region of the electrode structure, a variable equivalent resistance $R_E$ 1405 and a variable equivalent capacitance $C_E$ 1406, which represent the electrical properties of the electrolyte, and also the insulation or passivation layer 1104, in each case a resistance $R_M$ being connected in parallel with a capacitance $C_M$ and a resistance $R_E$ being connected in parallel with a capacitance $C_E$. As is furthermore shown in FIG. 14, the parallel circuit comprising components 1401, 1403, the parallel circuit comprising components 1402, 1404 and the parallel circuit comprising components 1405, 1406 are connected in series. The components 1401 to 1406 are represented as variable in order to illustrate that their values change owing to a sensor event.

According to an embodiment of the invention, the value which is characteristic of a hybridization event is the capacitance $C_M$. The value of the capacitance $C_M$ is determined from the required time duration for the charging and/or discharging of the at least one electrode 1101 of the sensor element 1100. An alteration of the value of the capacitance $C_M$ directly shows the biochemical event which is to be detected. The electrical properties of the electrolyte 1203 can be disregarded relative to the capacitance $C_M$. In accordance with these simplifications it becomes clear that it is necessary to distinguish between the contributions of the capacitance $C_M$ and the contributions of the resistance $R_M$. The extraction of the capacitance value $C_M$ is achieved in accordance with the device and the method of an embodiment of the present invention.

A description is given below, with reference to FIG. 15, of a sensor arrangement 1500 in accordance with a first example embodiment of the invention.

The sensor arrangement 1500 has the sensor element 1100, a current source 1501, a reference voltage source 1502, a comparator 1503, a first switch unit 1504 and a second switch unit 1505. The sensor element 1100 has two electrodes 1101, 1102 embodied as an interdigital structure. The voltage $V_A$ 1506 is present at a first electrode 1101 and the voltage $V_B$ 1507 is present at the other, i.e. the second, electrode 1102. Furthermore, the comparator 1503 has the terminals 1509, 1510, 1511 and 1512, wherein the terminals 1509 and 1511 are negative terminals and the terminals 1510 and 1512 are positive terminals, and the terminal 1510 is arranged between the terminals 1509 and 1511, and the terminal 1511 is arranged between the terminals 1510 and 1512. The first electrode 1101 is connected to the terminal 1509 and the second electrode 1102 is connected to the terminal 1512. The reference voltage source 1502 and the switch unit 1505 are arranged between the comparator 1503 and the sensor element 1100, wherein the switch unit 1505 is arranged between the reference voltage source 1502 and the comparator 1503, wherein a first terminal of the switch unit 1505 is connected to the terminal 1510 and a second terminal is connected to terminal 1511 of the comparator 1503. The sensor element 1100 is connected between the switch unit 1504 and the comparator 1503, the switch unit 1504 having two terminals 1513, 1514. The terminal 1513 is connected to the first electrode 1101 and the terminal 1514 is connected to the second electrode 1102. Furthermore, the switch unit 1504 is connected between the current source 1501 and the sensor element 1100.

A potential difference results from the charging operation and/or discharging operation of the electrodes 1101, 1102, the current source 1501 providing a predetermined electric current, that is to say a current that is predetermined in terms of the intensity and the direction, for the charging and/or discharging. The comparator 1503 compares the potential difference $(V_A-V_B)$ with the reference potential during the charging and/or discharging and transmits initialization signals for the changeover of the switch units to the respective switch unit if the value of the potential difference $(V_A-V_B)$ has reached the value of the reference potential. If the potential difference $(V_A-V_B)$ reaches the voltage value of the reference voltage source 1502 according to the magnitude, the flow direction of the current of the current source 1501 and the direction of the voltage of the reference voltage source 1502 are inverted by way of the switch unit 1504 and the switch unit 1505, the switch units 1504, 1505 in each case having two switches.

To put it another way, the first terminal 1519 of the current source 1501 is connected to the first electrode 1101 in a first switch position 1515 and the second terminal 1520 of the current source 1501 is connected to the second electrode 1102 in a first switch position 1517, as a result of which a predetermined current flows in the positive direction through the first electrode 1101 and a predetermined current flows in the negative direction through the second electrode 1102, whereby the first electrode 1101 is charged and the second electrode 1102 is discharged. After a changeover operation, the second terminal 1520 of the current source 1501 is connected to the first electrode 1101 in a second switch position 1516 and the first terminal 1519 of the current source 1501 is connected to the second electrode 1102 in a second switch position 1518, as a result of which a predetermined current flows in the negative direction through the first electrode and a current flows in the positive direction through the second electrode, whereby the first electrode 1101 is discharged and the second electrode 1102 is charged.

The direction of the reference voltage is changed over by way of the switch unit 1505 in a manner corresponding to the switch positions 1515, 1516, 1517 and 1518. During the charging operation, a first terminal 1525 of the reference voltage source 1502 is connected to the positive terminal 1510 of the comparator 1503 in a first switch position 1521 and a second terminal 1526 of the reference voltage source 1502 is connected to the negative terminal 1511 of the comparator 1503 in a first switch position 1523. During a discharging operation, a first terminal 1525 of the reference voltage source 1502 is connected to the negative terminal 1511 of the comparator 1503 in a second switch position 1522 and a second terminal 1526 of the reference voltage source 1502 is connected to the positive terminal 1510 of the comparator 1503 in a second switch position 1524.

The respective switch positions are obtained by way of initialization signals which are correspondingly transmitted by the comparator.

Figure 15:
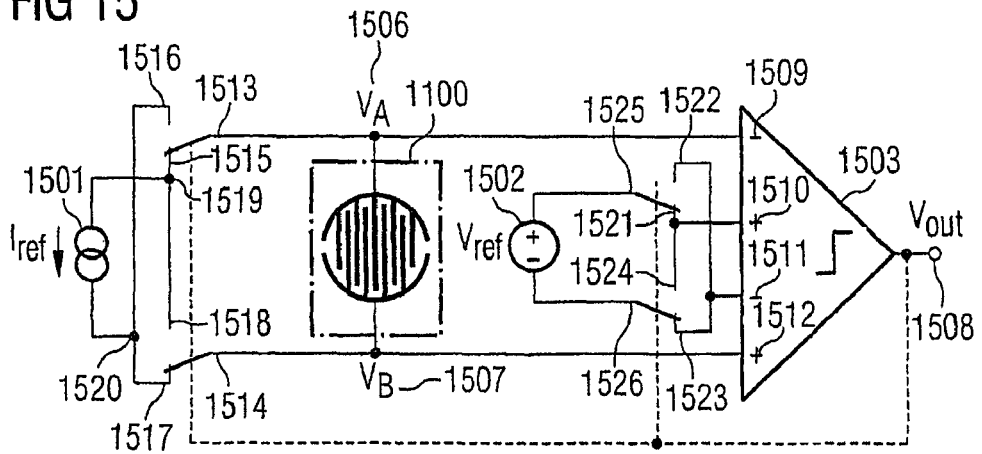
FIG. 15 shows a sensor arrangement in accordance with a first example embodiment of the invention.

As a result, the electrodes 1101, 1102 of the example embodiment shown in FIG. 15 are oppositely charged and/or discharged and the charging operation and/or discharging operation starts anew. After each changeover operation, the comparator 1503 outputs a signal in the form of a voltage $V_{out}$ 1508, the output signal of the comparator being a digital signal.

Figure 16:
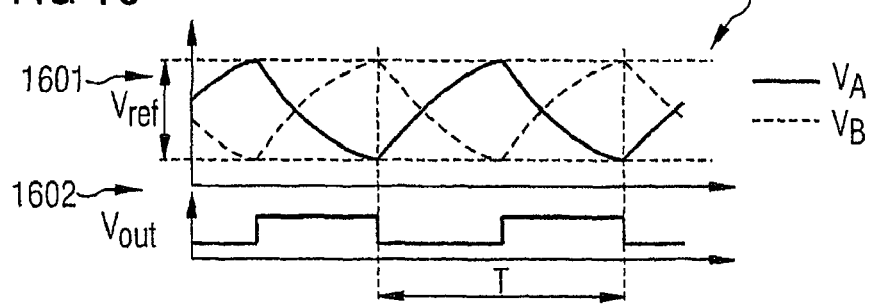
FIG. 16 shows the profile of voltage signals when carrying out a measurement.

FIG. 16 shows a voltage diagram 1600 resulting from operation in each case for the potential difference 1601 between the first electrode 1101 and the second electrode 1102 of the sensor element 1100 and for the signal output voltage 1602 of the comparator 1503. The voltage diagram 1601 shows the opposite charging or discharging of the first electrode 1101 and of the second electrode 1102. The voltages $V_A$ and $V_B$ are the voltages which were explained in FIG. 15. If the first electrode 1101 is charged, the value of the voltage profile rises up to the reference voltage. At the same time, the second electrode 1102 is discharged to the same extent, as a result of which the two voltage profiles of the voltages $V_A$ and $V_B$ have the same but an inverted profile, wherein the voltage profile has a zigzag profile.

A description is given below, with reference to FIG. 17, of a detailed view of the sensor arrangement 1500 of the preferred embodiment shown in FIG. 15.

Figure 17:
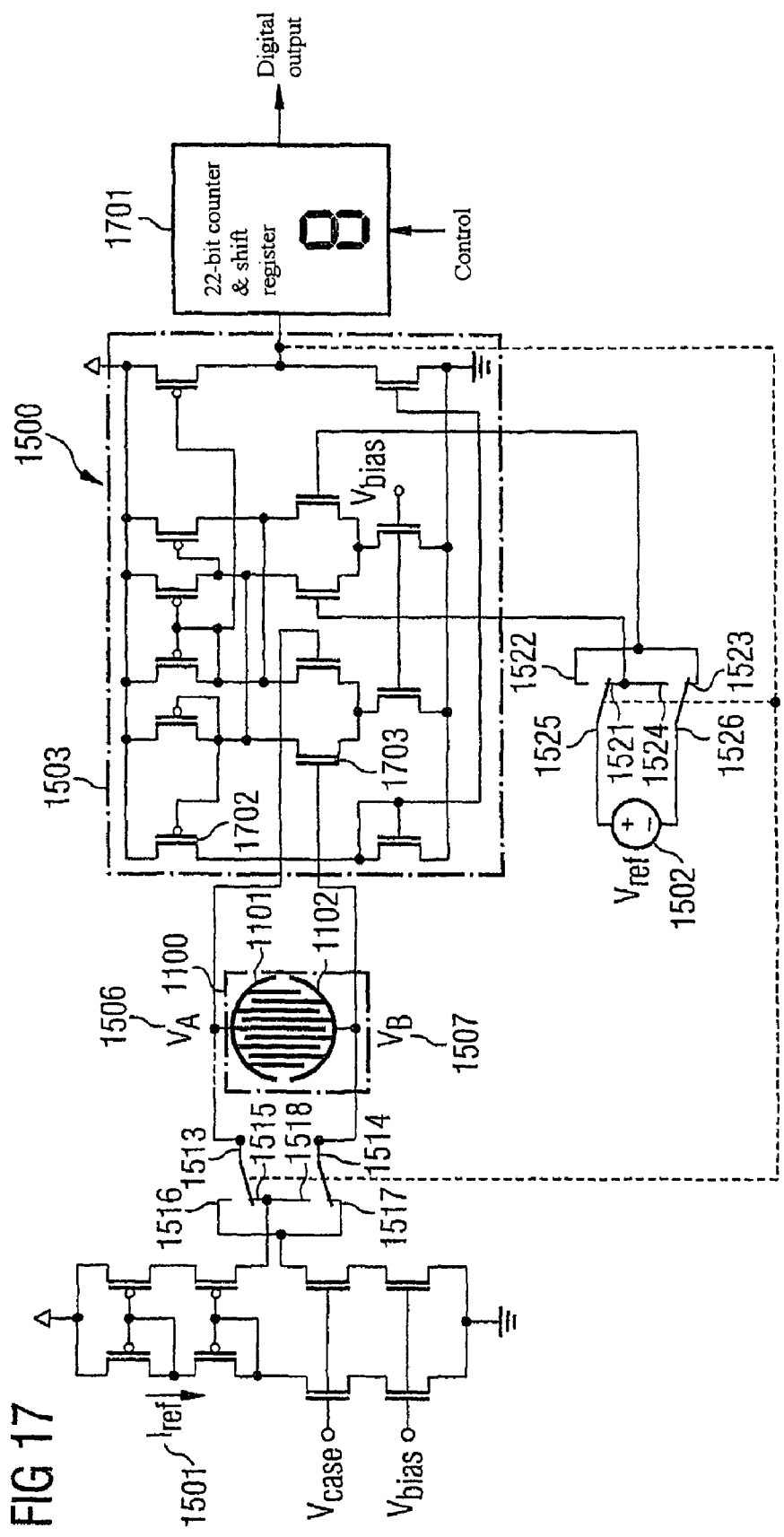
FIG. 17 shows an equivalent circuit diagram of the sensor arrangement in accordance with the first embodiment of the invention as shown in FIG. 15.

The sensor arrangement in accordance with FIG. 17 has the same switching structure of the sensor arrangement shown in FIG. 15, the voltage source 1501, the sensor element 1100, the reference voltage source 1502, the comparator 1503, the first switch unit 1504, the second switch unit 1505 and a counter 1701, the counter 1701 being formed as a shift register. The comparator 1503 has a circuit arrangement having transistors 1702 and transistors 1703. The constant-current source 1501, which provides a predetermined current, likewise has a circuit arrangement having transistors 1702 and transistors 1703.

According to an embodiment of the present invention, the counter 1701 counts in a given time duration the number of digital output signals of the comparator 1503 which in each case correspond to a changeover operation. A charging operation or discharging operation corresponds to the temporal succession of two signals of the comparator 1503. The fact of whether a sensor event has taken place is determined from the time duration required for the charging and/or discharging. The value of a capacitance C corresponding to the sensor event is determined from said time duration in accordance with the equations described above, a lower threshold value and an upper threshold value for the capacitance being determined empirically depending on the analyte and on the sensor arrangement. If the value of the capacitance determined lies within these two limit values, a sensor event has occurred.

A description is given below, with reference to FIG. 18, of a sensor arrangement in accordance with a second embodiment of the invention.

The sensor arrangement 1800 has the sensor element 1100, the first electrode 1101, the second electrode 1102, a first current source 1801, a second current source 1802, a first reference voltage source 1803, a second reference voltage source 1804, a comparator 1805, a first switch unit 1806, a second switch unit 1807 and a device for the provision of a reference-ground potential 1808. The comparator 1805 has a positive terminal 1809, to which the first electrode 1101 of the sensor element 1100 is connected, and a negative terminal 1810, to which the switch unit 1807 is connected. The voltage sources 1803, 1804 are connected to the switch unit 1807 by a respective terminal, the switch unit 1807 changing over between the voltage source 1803, 1804. Furthermore, the two voltage sources 1803, 1804 supply reference potentials having an opposite sign. The voltage sources 1803, 1804 are connected to the second electrode 1102 of the sensor element 1100 by a second terminal. Consequently, the switch unit 1807 is connected between the comparator 1805 and the voltage sources 1803, 1804.

In accordance with the second example embodiment, a predetermined reference-ground potential 1808 is applied to one of the electrodes 1102 of the sensor element 1100. The other electrode 1101 of the sensor element 1100 is periodically charged and/or discharged in accordance with the means of the complementary current sources 1801 and 1802, the comparator 1805 comparing the voltage $V_A$ 1506 of the electrode 1101 during the charging operation and/or discharging operation with either the reference voltage of the voltage source 1803 or with the reference voltage of the voltage source 1804. If the voltage 1506 of the electrode 1101 reaches one of the reference voltages of the voltage sources 1803, 1804, then for example the charging operation is ended and the electrode 1101 is discharged.

During a charging operation, a first terminal 1815 of the current source 1801 is connected to the first electrode 1101 via a first switch position 1811 of the switch unit 1806 and a second terminal 1816 of the current source 1801 is connected to a predetermined reference-ground potential, whereby the first electrode 1101 is charged with a predetermined current, the current flow direction being directed from the predetermined reference-ground potential to the switch unit 1806.

During a discharging operation, a first terminal 1817 of the current source 1802 is connected to the first electrode 1101 via a second switch position 1812 of the switch unit 1806 and a second terminal 1818 of the current source 1802 is connected to a predetermined reference-ground potential, whereby the first electrode 1101 is discharged with a predetermined current, the current flow direction being directed from the switch unit 1806 to the predetermined reference-ground potential.

During a charging operation, the second electrode 1102 is connected to the reference voltage of the voltage source 1803 by way of a first switch position 1813 of the switch unit 1807. During a discharging operation, the second electrode 1102 is connected to the reference voltage of the voltage source 1804 by way of a second switch position 1814 of the switch unit 1807.

The corresponding switch positions are assumed by way of initialization signals transmitted to the switch unit 1806, 1807 by the comparator 1805.

A description is given below, with reference to FIG. 19, of a sensor arrangement 1900 in accordance with a third embodiment of the invention.

Figure 18:
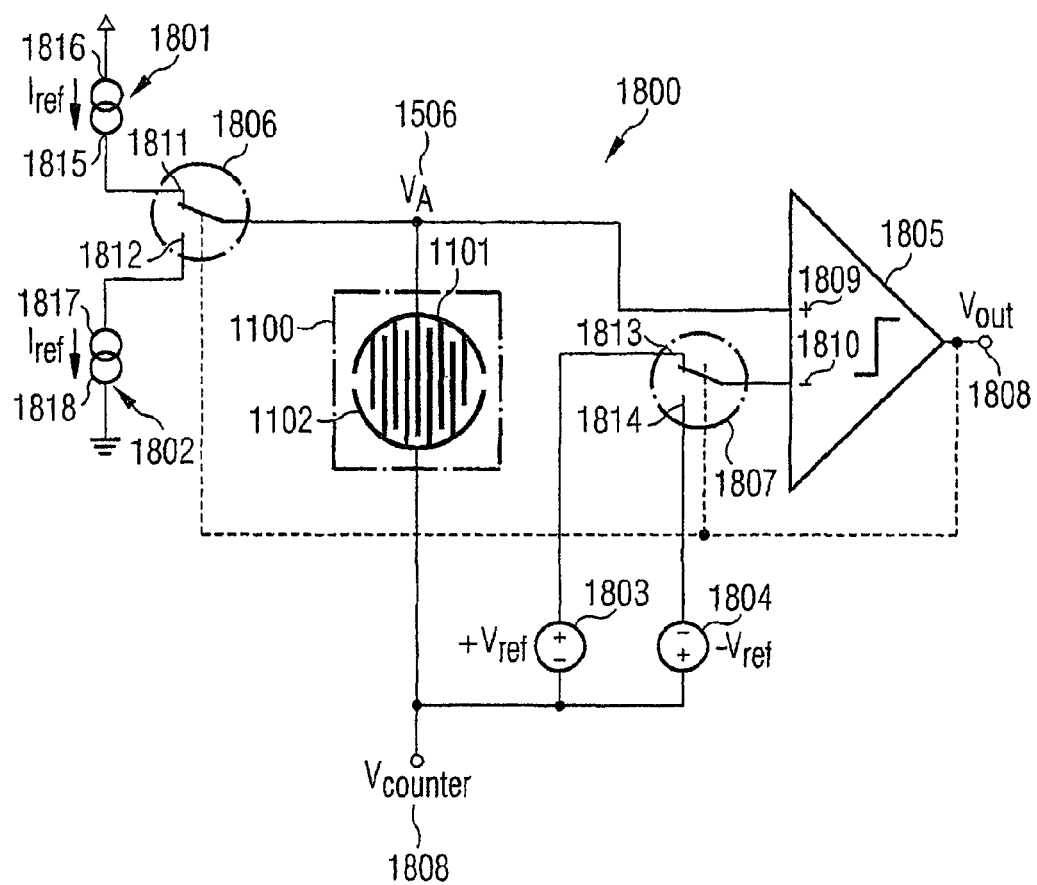
FIG. 18 shows a simplified sensor arrangement in accordance with the second embodiment of the invention.
Figure 19:
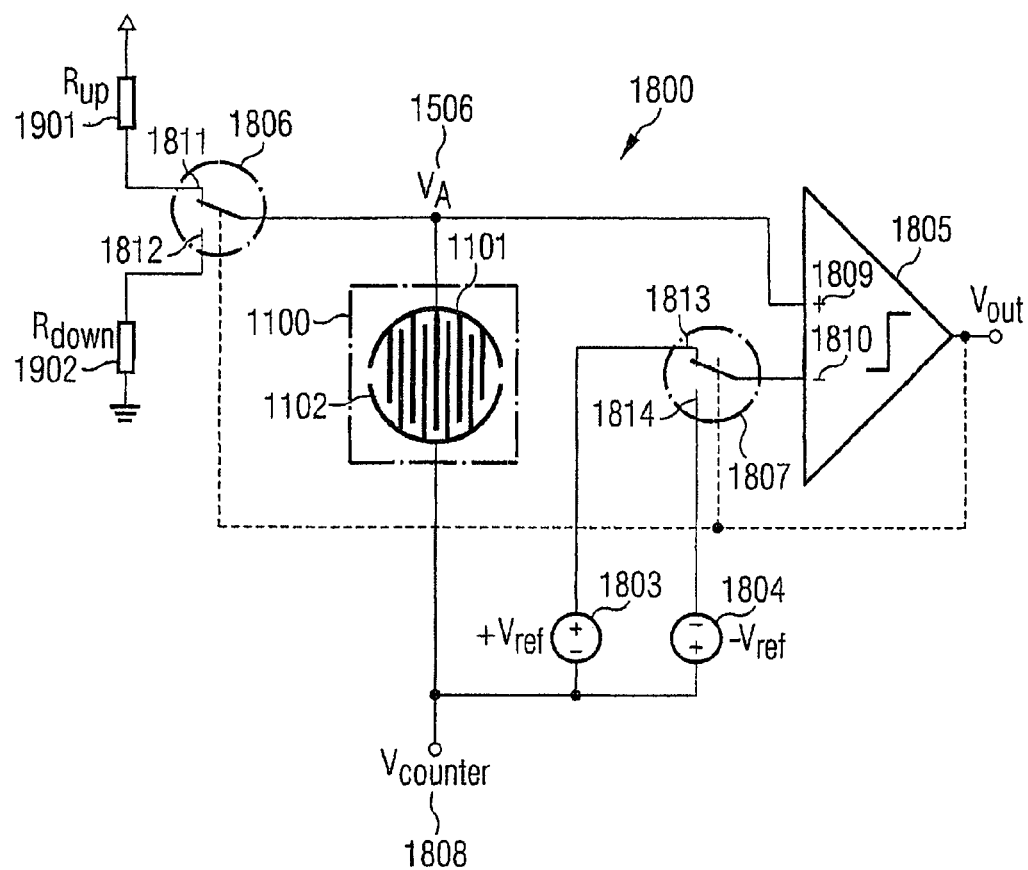
FIG. 19 shows a sensor arrangement in accordance with a third embodiment of the invention.

The sensor arrangement of FIG. 19 is similar to the sensor arrangement of FIG. 18. The two current sources 1801 and 1802 are replaced by a resistance $R_{up}$ 1901 and a resistance $R_{down}$ 1902, respectively. The constant-current sources are not absolutely necessary provided that the current for the charging and/or discharging of the electrodes can be derived, in which case the current can be derived from Ohm's law with regard to the use of the resistances 1901, 1902.

In accordance with the sensor arrangement 1900, it is therefore necessary to correspondingly adapt the equations (5)

$$\frac{1}{f} = T = 2R_{sensor}C_{sensor}\ln\frac{1}{1-\frac{V_{ref}}{I_{ref}R_{sensor}}} \tag{5}$$

and (6)

$$C = -\frac{1}{2V_{ref}\frac{\partial}{\partial I_{ref}}\left[\left(I_{ref}\frac{\partial T}{\partial I_{ref}}\right)^{-1}\right]}, \tag{6}$$

which were described above, for the calculation of the impedance 1202.

A description is given below, with reference to FIG. 20, of a simplified sensor arrangement 2000 of the example embodiment shown in FIG. 5.

Figure 1:
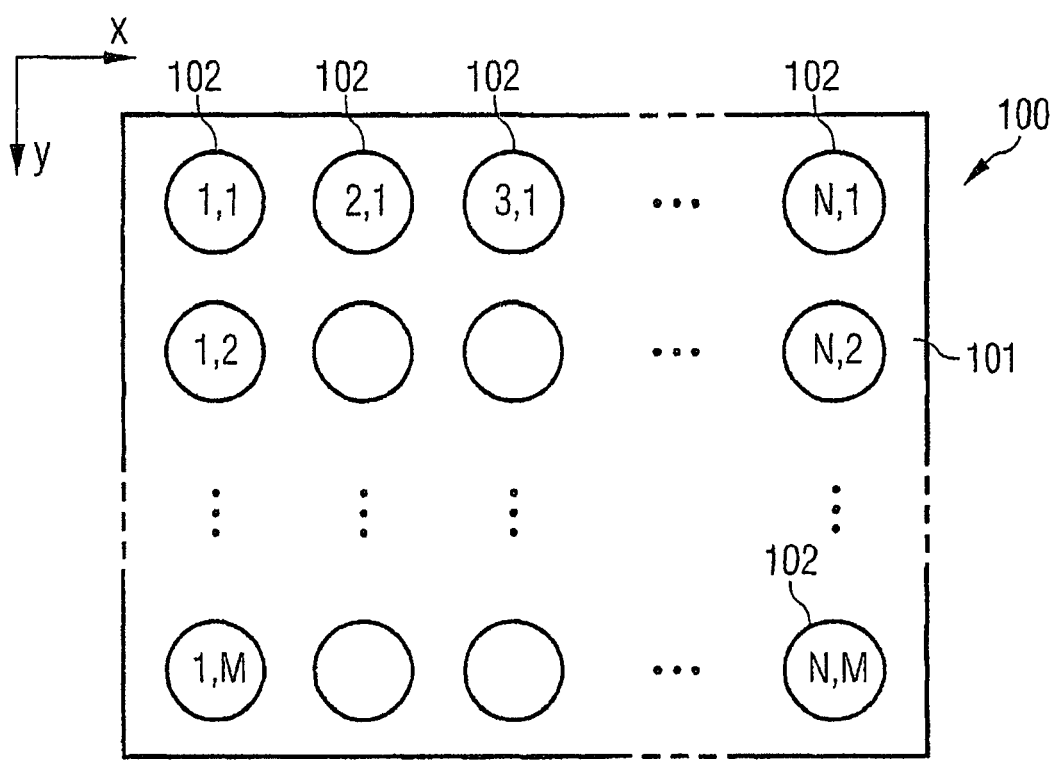
FIG. 1 shows a sensor arrangement in accordance with the prior art.
Figure 2A:
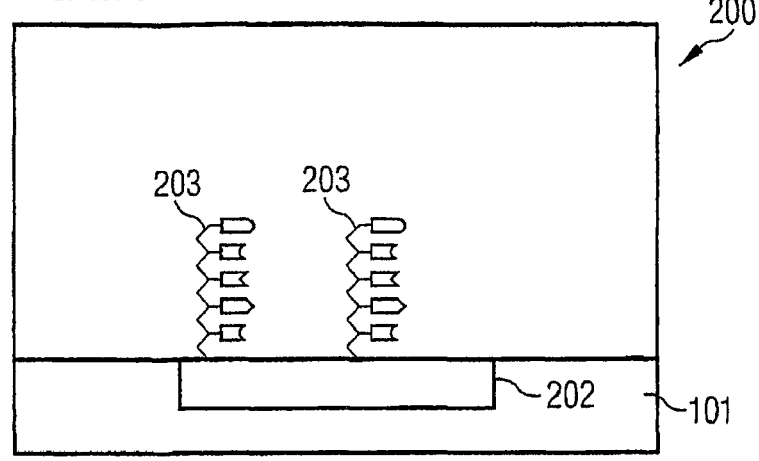
FIGS. 2A to 2F show cross-sectional views of a partial region of the sensor arrangement shown in FIG. 1 at different points in time during a method for operating the sensor arrangement.
Figure 2B:
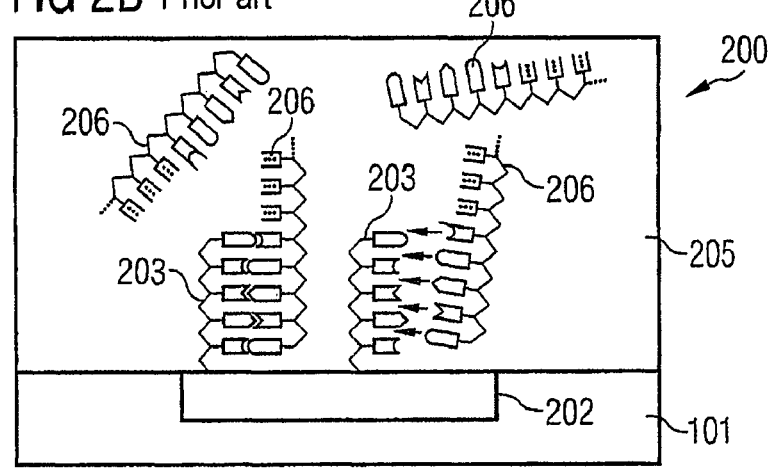
Figure 2C:
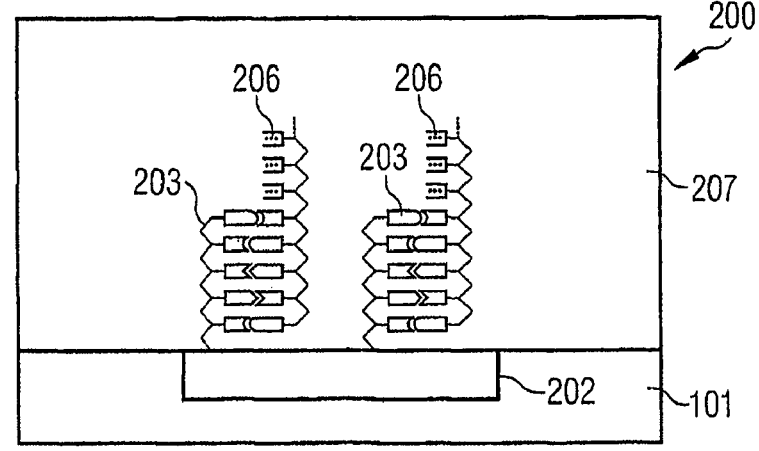
Figure 2D:
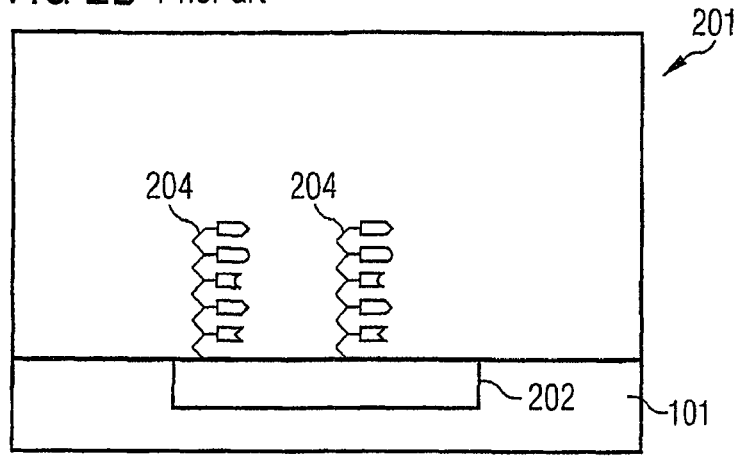
Figure 2E:
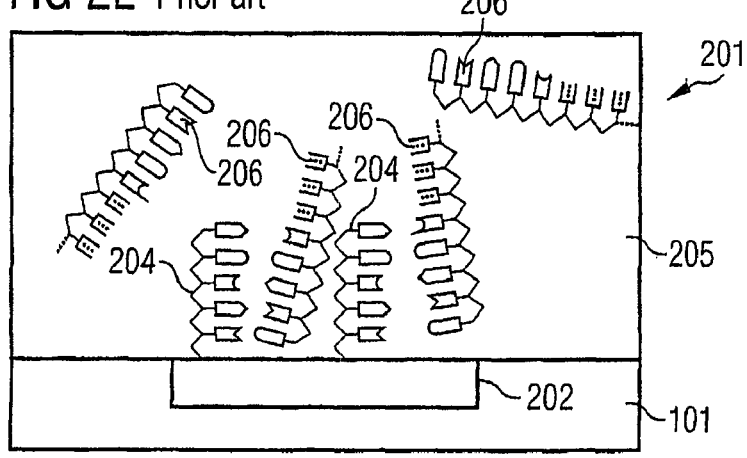
Figure 2F:
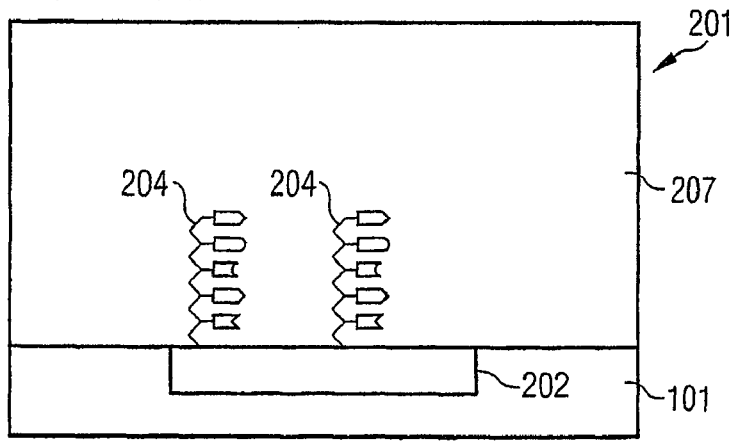
Figure 3A:
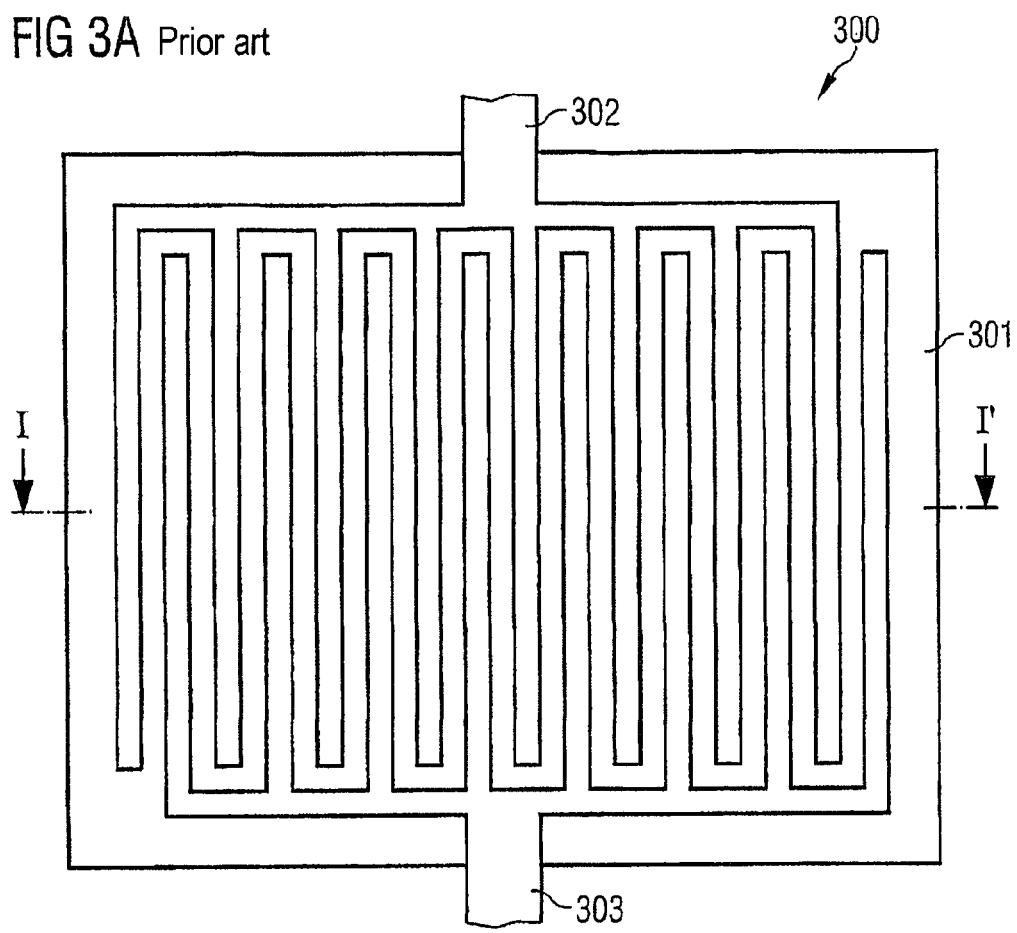
FIGS. 3A, 3B show a plan view and a cross-sectional view along the section line I-I' of an interdigital electrode arrangement in accordance with the prior art.
Figure 3B:
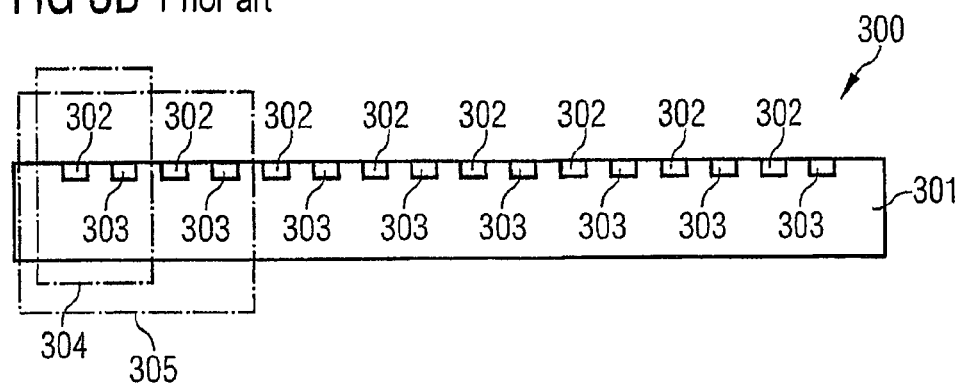
Figure 4A:
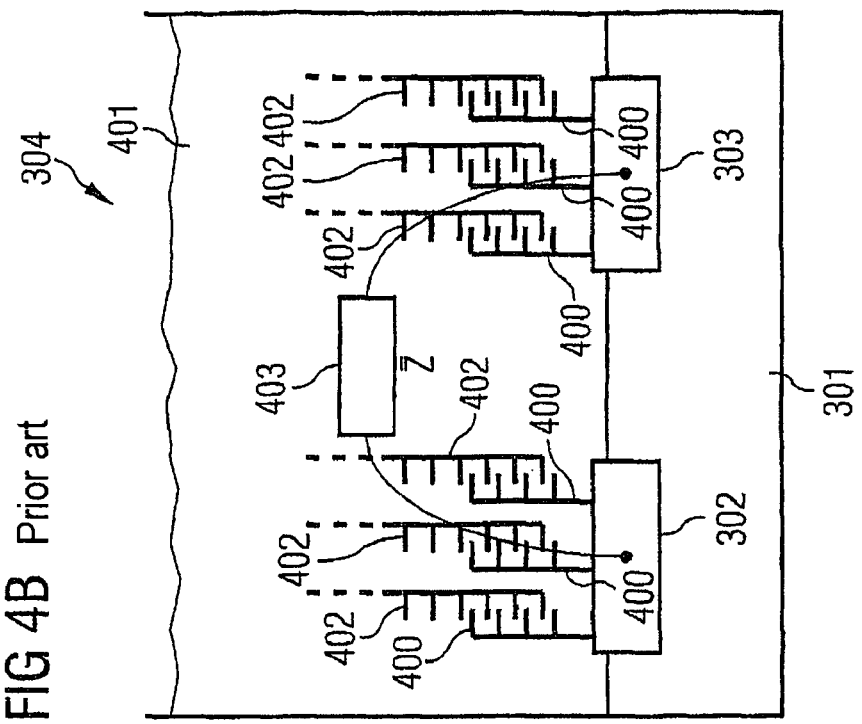
FIGS. 4A, 4B show cross-sectional views of a first partial region of the interdigital electrode arrangement shown in FIG. 3 at different points in time during a method for operating the interdigital electrode arrangement in accordance with the prior art.
Figure 4B:
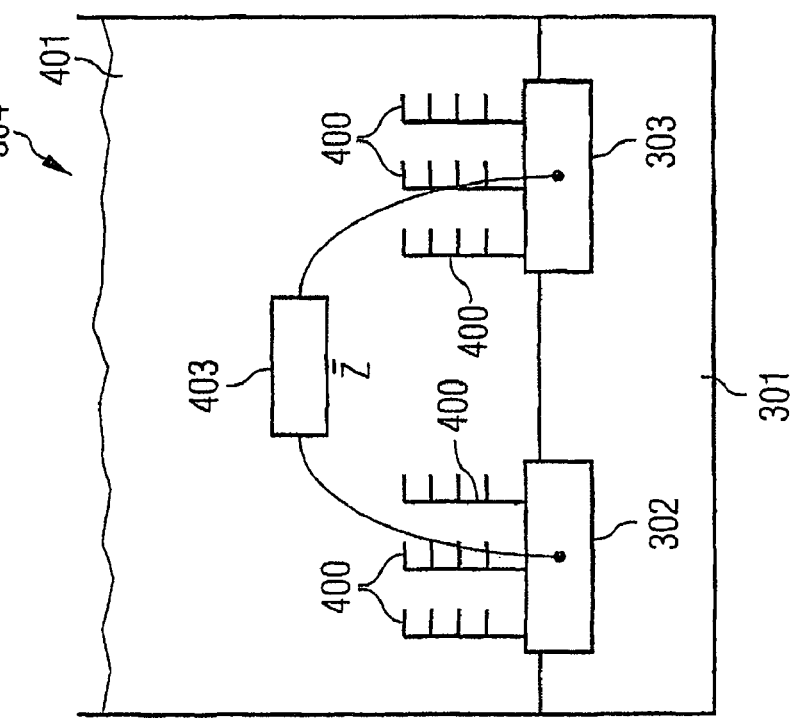
Figure 5:
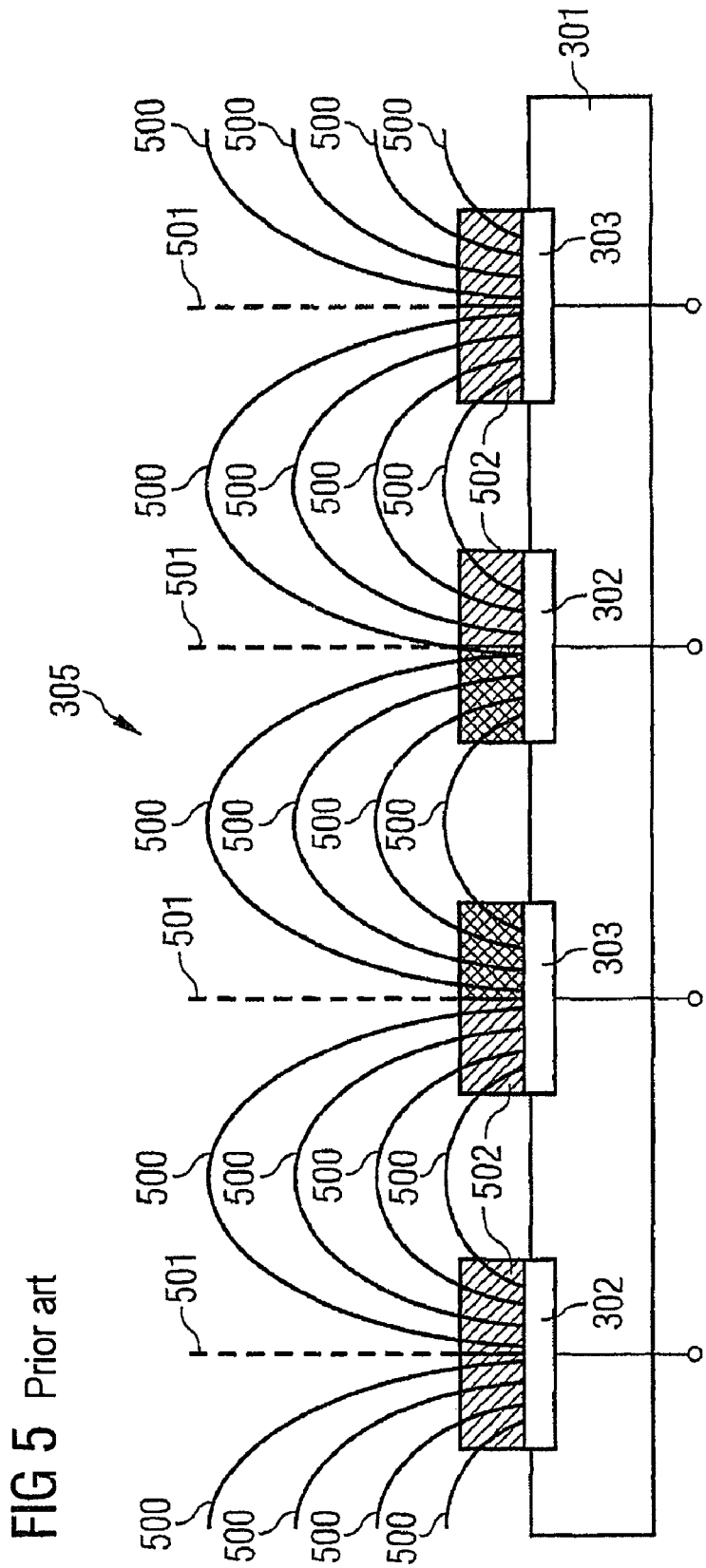
FIG. 5 shows a cross-sectional view of a second partial region of the interdigital electrode arrangement in accordance with the prior art as shown in FIG. 3.
Figure 6:
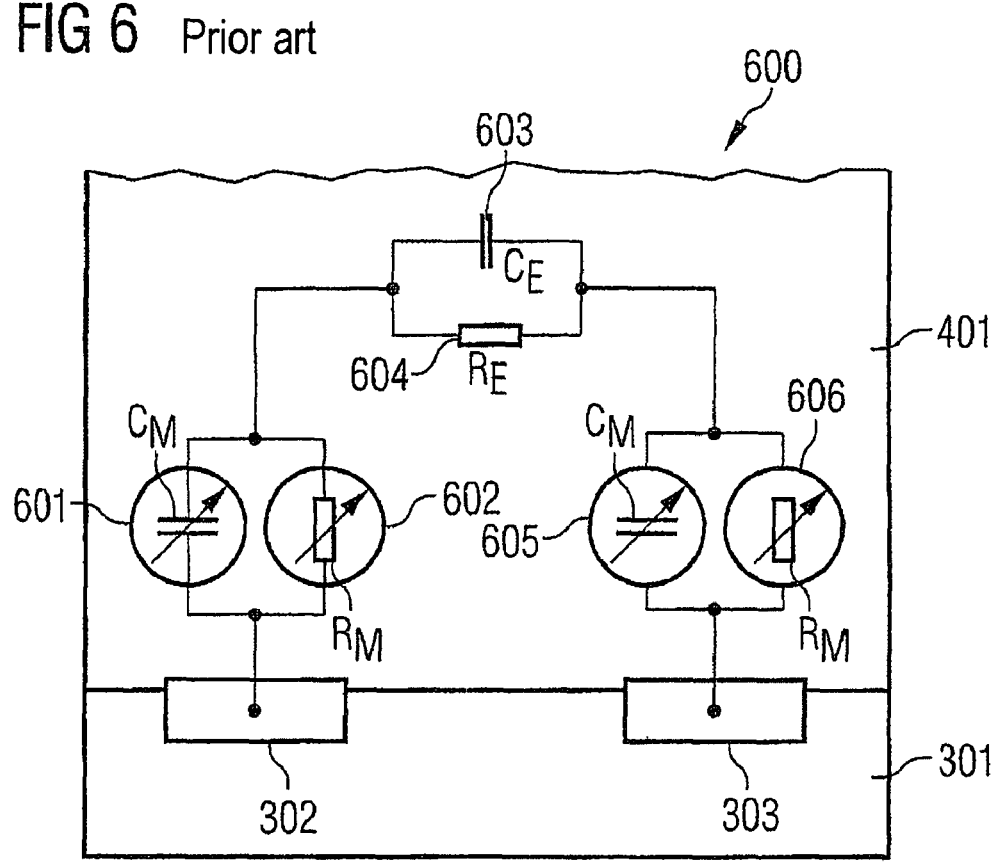
FIG. 6 shows an equivalent circuit diagram of the first partial region of the interdigital electrode arrangement from FIG. 3 in accordance with the prior art.
Figure 8A:
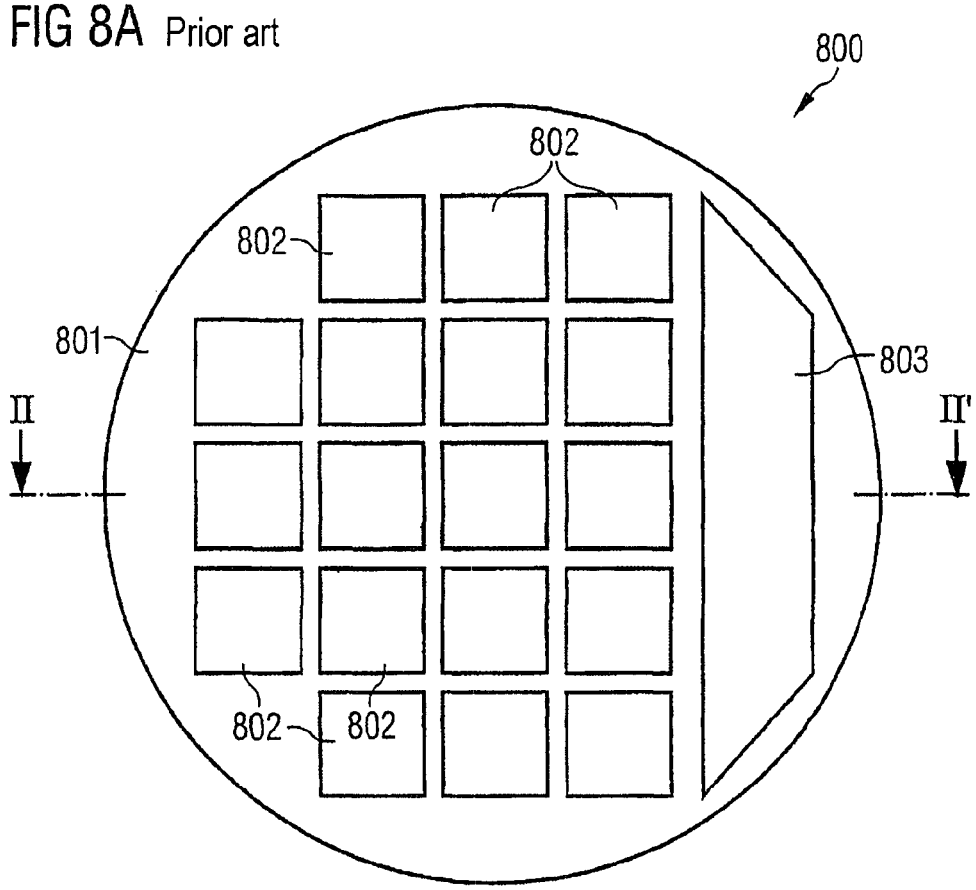
Figure 8B:
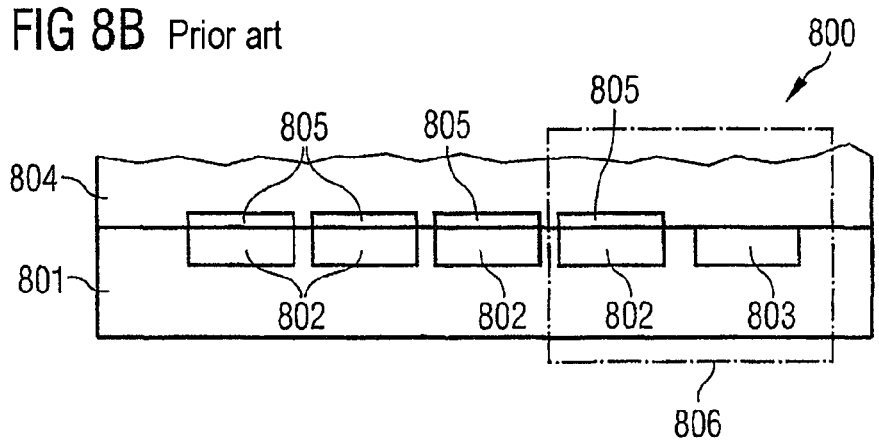
Figure 9:
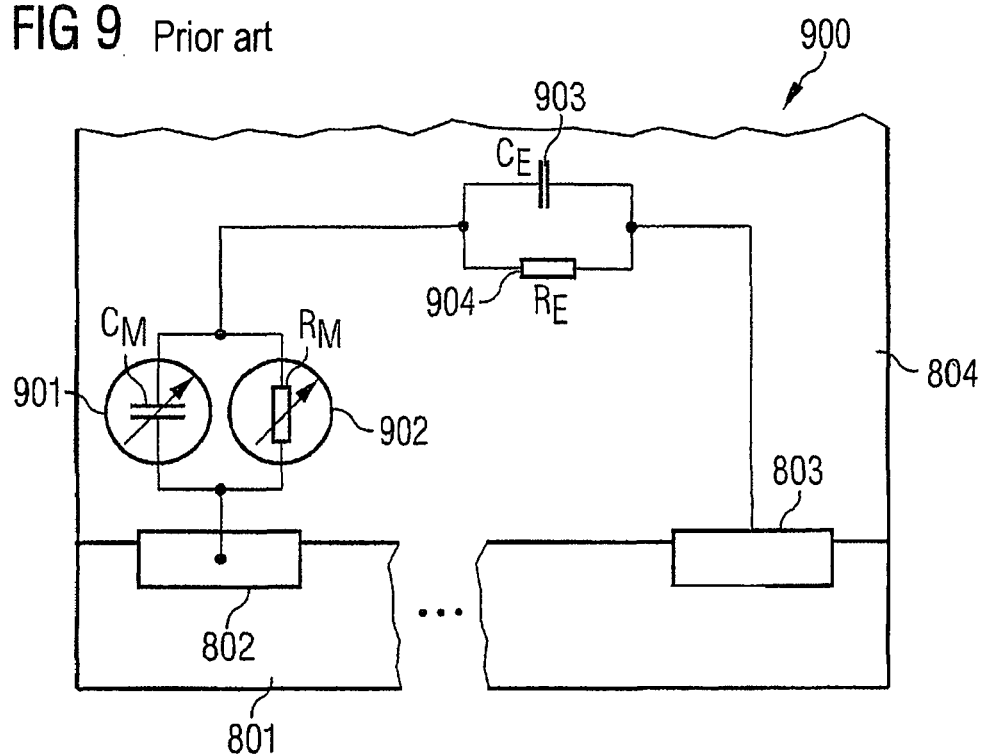
FIG. 9 shows an equivalent circuit diagram of the sensor arrangement from FIG. 8 in accordance with the prior art.
Figure 10:
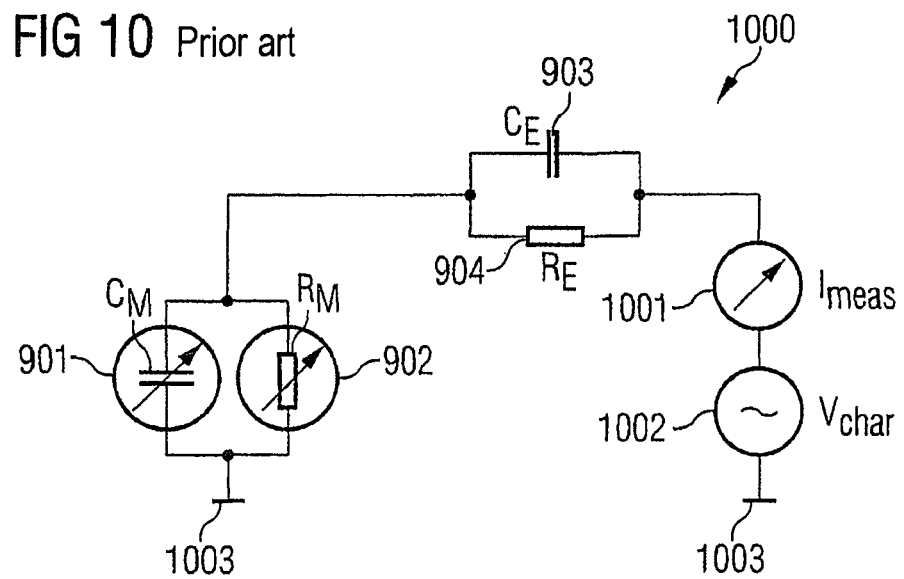
FIG. 10 shows another equivalent circuit diagram of the sensor arrangement from FIG. 8 in accordance with the prior art.

The sensor arrangement 2000 has the same elements of the sensor arrangement shown in FIG. 5. In accordance with this example embodiment, however, the circuit arrangement has been varied for reasons of simplification. The reference voltage source 1502 is directly connected to the comparator 1503, the reference voltage source 1502 being arranged between the current source 1501 and the comparator 1503. One terminal of the current source 1501 is connected to the negative terminal 1509 and the other terminal is connected to the positive terminal 1512 of the comparator 1503, the current source 1501 being arranged between the switch unit 1504 and the comparator 1503.

One terminal of the switch unit 1504 is connected to the terminal 1509 and the other terminal is connected to the terminal 1512 of the comparator 1503, the switch unit 1504 being arranged between the sensor element 1100 and the comparator 1503. The switch unit 1504 is rotated through 180° about the longitudinal axis relative to the sensor arrangement 1500 shown in FIG. 15. Consequently, the first electrode 1101 of the sensor element 1100 is connected to the terminal 1513 of the switch unit 1504 and the second electrode 1102 of the sensor element 1100 is connected to the terminal 1514 of the switch unit 1504.

In accordance with this embodiment, the current flow direction of the current source 1501 and the direction of the reference voltage of the reference voltage source 1502 are not periodically changed over by means of the switch unit 1504, but rather the flow direction of the current by way of the switch unit 1504 directly at the electrodes 1101, 1102 of the sensor element.

To put it another way, the first terminal 1519 of the current source 1501 is connected to the first electrode 1101 in a first switch position 1515 and the second terminal 1520 of the current source 1501 is connected to the second electrode 1102 in a first switch position 1517, as a result of which a predetermined current flows in the positive direction through the first electrode 1101 and a predetermined current flows in the negative direction through the second electrode 1102, whereby the first electrode 1101 is charged and the second electrode 1102 is discharged. After a changeover operation, the second terminal 1520 of the current source 1501 is connected to the first electrode 1101 in a second switch position 1516 and the first terminal 1519 of the current source 1501 is connected to the second electrode 1102 in a second switch position 1518, as a result of which a predetermined current flows in the negative direction through the first electrode and a current flows in the positive direction through the second electrode, whereby the first electrode 1101 is discharged and the second electrode 1102 is charged.

The respective switch positions are obtained by way of initialization signals which are correspondingly transmitted by the comparator.

During the charging and/or discharging, the comparator 1503 compares the reference voltage of the reference voltage source 1502 with the potential difference $(V_A-V_B)$ of the sensor element 1100 until the potential difference $(V_A-V_B)$ corresponds to the reference voltage before a next changeover operation is initialized.

In order to minimize the switching operations within the circuit arrangement, only the electrodes 1101, 1102 of the sensor element 1100 are periodically changed over.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The following publications are cited in this document:
[1] M. Paeschke et al., Electroanalysis 1996, 7, No. 1, pp. 1-8
[2] R. Hintzsche et al., "Microbiosensors using electrodes made in Si-technology", in "Frontiers in Biosensorics I—Fundamental Aspects", F. W. Scheller et al. ed., 1997, Birkhauser Verlag Basel
[3] WO 9322678
[4] DE 19610115 A1
[5] U.S. Patent Ser. No. 60/007,840
[6] Peter Van Gerwen et al., Transducers '97, pp. 907-910
[7] Christian Krause et al., Langmuir, Vol. 12, No. 25, 1996 pp. 6059-6064
[8] V. M. Mirsky, Biosensors & Bioelectronics 1997, Vol. 12 No. 9-10, pp. 977-989
[9] M. Riepl et al., Mikrochim. Acta, 29-34, 1999
[10] U.S. Pat. No. 6,170,318 B1

LIST OF REFERENCE SYMBOLS

1100 Sensor element
1101 First electrode of the sensor element
1102 Second electrode of the sensor element
1103 Insulation or passivation layer
1104 Cross-sectional view of the sensor element
1105 Finger of the first electrode
1106 Finger of the second electrode
1200 Cross-sectional view of the sensor element
1201 Catcher molecules
1202 Impedance
1203 Electrolyte
1204 Cross-sectional view of the sensor element
1205 Particles to be detected
1300 Cross-sectional view of the sensor element
1301 Profile of the electric field
1400 Cross-sectional view of the sensor element
1401 Variable nonreactive resistance
1402 Variable nonreactive resistance
1403 Variable capacitance
1404 Variable capacitance
1405 Variable nonreactive resistance
1406 Variable capacitance
1500 Sensor arrangement
1501 Current source
1502 Reference voltage source
1503 Comparator
1504 First switch unit
1505 Second switch unit
1506 Voltage of the first electrode
1507 Voltage of the second electrode
1508 Output voltage of the comparator
1509 First negative terminal of the comparator
1510 First positive terminal of the comparator
1511 Second negative terminal of the comparator
1512 Second positive terminal of the comparator
1513 First terminal of the first switch unit
1514 Second terminal of the first switch unit
1515 First switch position of the first switch unit
1516 Second switch position of the first switch unit
1517 First switch position of the first switch unit
1518 Second switch position of the first switch unit
1519 First terminal of the current source
1520 Second terminal of the current source
1521 First switch position of the second switch unit
1522 Second switch position of the second switch unit
1523 First switch position of the second switch unit
1524 Second switch position of the second switch unit
1525 First terminal of the reference voltage source
1526 Second terminal of the reference voltage source
1600 Diagram of the voltage profiles
1601 Voltage diagram of the sensor voltage
1602 Voltage diagram of the output voltage of the comparator
1700 Detailed view of the sensor arrangement
1701 Counter
1702 Transistors
1703 Transistors
1800 Example embodiment of the sensor arrangement
1801 First current source
1802 Second current source
1803 First reference voltage source
1804 Second reference voltage source
1805 Comparator
1806 First switch unit
1807 Second switch unit
1808 Reference-ground potential
1809 Positive terminal of the comparator
1810 Negative terminal of the comparator
1811 First switch position of the first switch unit
1812 Second switch position of the first switch unit 1813 First switch position of the second switch unit
1814 Second switch position of the second switch unit
1815 First terminal of the first current source
1816 Second terminal of the first current source
1817 First terminal of the second current source
1818 Second terminal of the second current source
1900 Preferred embodiment of the sensor arrangement
1901 First nonreactive resistance
1902 Second nonreactive resistance
2000 Example embodiment of the sensor arrangement

The invention claimed is:

1. A sensor arrangement, comprising:
   at least one electrode;
   a sensor element dependent on a sensor event in terms of its profile, at the at least one electrode;
   a drive circuit, to provide an electric current source at a constant magnitude as a predetermined electric current, the at least one electrode being at least one of charged and discharged with the predetermined electric current;
   a comparator unit, to compare the electrical voltage provided by the sensor element with a reference voltage, and to provide a comparison result;
   a voltage source, to provide the reference voltage to the comparator, the voltage source being coupled to the comparator unit;
   an evaluation circuit that receives an output signal from the comparator unit, to determine a time duration required for the at least one of charging and discharging of the electrode, from at least one of a predetermined voltage to the reference voltage and from the reference voltage to the predetermined voltage, the time duration representing at least one of whether or not a sensor event has taken place and the extent to which a sensor event has taken place at the sensor element;
   a switch unit, configured to invert a flow direction of the current from the drive circuit, the switch unit being connected between the drive circuit and the comparator unit, the electrode being charged or discharged depending on the switch state; and
   a control unit for controlling the switch unit such that, by way of the switch unit, with changeover of the switch unit, the electrode is repeatedly at least one of charged from the predetermined voltage to the reference voltage and discharged from the reference voltage to the predetermined voltage, wherein the sensor element is connected between the switch unit and the comparator.

2. The sensor arrangement as claimed in claim 1, wherein the sensor element includes at least two electrodes mounted thereon.

3. The sensor arrangement as claimed in claim 2, wherein the at least two electrodes are arranged such that the two electrodes intermesh in comb-type fashion.

4. The sensor arrangement as claimed in claim 2, wherein two electrodes are arranged such that the two electrodes intermesh in comb-type fashion, and wherein a third electrode is arranged in meandering fashion between the two electrodes.

5. The sensor arrangement as claimed in claim 1, wherein the comparator unit is a comparator.

6. The sensor arrangement as claimed in claim 1, wherein the control unit is set up such that the switch state of the switch unit is changed over if the voltage of the electrode is the reference voltage or the predetermined voltage.

7. The sensor arrangement as claimed in claim 1, further comprising a sensor event determining unit, configured to determine whether a sensor event has taken place is determined from the determined time durations of at least one of the charging operation and the discharging operation.

8. The sensor arrangement as claimed in claim 7, wherein the sensor event determining unit is set up in such a way that at least one of a charging frequency and a discharging frequency and a cycle frequency, where a cycle in each case has a charging operation and a discharging operation, is determined from the determined time durations of at least one of the charging operation and of the discharging operation.

9. The sensor arrangement as claimed in claim 1, wherein the sensor element is set up as a biosensor element for the detection of biomolecules.

10. The sensor arrangement as claimed in claim 1, further comprising a plurality of sensor elements.

11. The sensor arrangement as claimed in claim 9, wherein the sensor elements are arranged in matrix-type fashion.

12. The sensor arrangement as claimed in claim 1, wherein the sensor event is a hybridization event.

13. The sensor arrangement as claimed in claim 1, further comprising a further switch unit between the sensor element and the comparator, wherein the drive circuit is directly connected to the switch unit and the further switch unit is directly connected to the voltage source and the comparator.

14. A method for determining a sensor event at a sensor element, the method comprising:
   at least one of charging and discharging at least one electrode by way of a predetermined electric current at a constant magnitude;
   determining a time duration required for the at least one of charging and discharging of the electrode, at least one of from a predetermined voltage generated by a drive circuit to a reference voltage generated by a voltage source arranged between a comparator and the sensor element and from the reference voltage to the predetermined voltage, the time duration being dependent on at least one of whether or not a sensor event has taken place at the sensor element, connected between the drive circuit and the comparator and the extent to which a sensor event has taken place at the sensor element; and
   using the determined time duration to determine whether a hybridization event has taken place.

15. A sensor arrangement, comprising:
   at least one electrode;
   a sensor element dependent on a sensor event in terms of its profile, at the at least one electrode;
   a drive circuit, to provide an electric current source at a constant magnitude as a predetermined electric current, the at least one electrode being at least one of charged and discharged with the predetermined electric current;
   a comparator unit, to compare the electrical voltage provided by the sensor element with a reference voltage, and to provide a comparison result;
   a voltage source, to provide a reference voltage to the comparator, the voltage source being coupled to the comparator unit;
   an evaluation circuit that receives an output signal from the comparator unit, to determine a time duration required for the at least one of charging and discharging of the electrode, from at least one of a predetermined voltage to the reference voltage and from the reference voltage to the predetermined voltage, the time duration representing at least one of whether or not a sensor event has taken place and the extent to which a sensor event has taken place at the sensor element; and
   a switch unit directly connected to the voltage source and the comparator.

* * * * *